(12) United States Patent
Xiao et al.

(10) Patent No.: US 9,822,392 B2
(45) Date of Patent: Nov. 21, 2017

(54) CO-TRANSLATIONAL ACTIVATION OF A TRANSCRIPTION FACTOR BY PROTEOLYTIC CLEAVAGE AND METHODS OF USE

(71) Applicant: The Johns Hopkins University, Baltimore, MD (US)

(72) Inventors: Jie Xiao, Baltimore, MD (US); Zachary Hensel, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 160 days.

(21) Appl. No.: 14/317,631

(22) Filed: Jun. 27, 2014

(65) Prior Publication Data
US 2015/0010925 A1 Jan. 8, 2015

Related U.S. Application Data

(60) Provisional application No. 61/840,891, filed on Jun. 28, 2013.

(51) Int. Cl.
*C12Q 1/37* (2006.01)
(52) U.S. Cl.
CPC ............ *C12Q 1/37* (2013.01); *C07K 2319/50* (2013.01); *C07K 2319/60* (2013.01)
(58) Field of Classification Search
CPC ... C07K 2319/60; C07K 2319/50; C12Q 1/37
See application file for complete search history.

(56) References Cited

PUBLICATIONS

Heinzel, T., et al., 1994, "C1 repressor-mediated DNA looping is involved in C1 autoregulation of bacteriophage P1", The Journal of Biological Chemistry, vol. 269, No. 50, pp. 31885-31890.*
Ozbudak, E.M., et al., 2002 "Regulation of noise in the expression of a single gene", Nature Genetics, vol. 31, No. 1, pp. 69-73.*
Dodd, I.B., et al., 2004, "Cooperativity in long-range gene regulation by the lambda CI repressor", Genes and Development, vol. 18, No. 3. pp. 344-354.*
Golding, I., et al., 2005, "Real-time kinetics of gene activity in individual bacteria", Cell, vol. 123, No. 6, pp. 1025-1036.*
Yu, J., et al., 2006, "Probing gene expression in live cells, one protein molecule at a time", Science, vol. 311, No. 5767, pp. 1600-1603.*
Taniguchi, Y., et al., 2010, "Quantifying *E. coli* proteome and transcriptome with single molecule sensitivity in single cells", Science, vol. 329, No. 5991, pp. 533-538.*
So, L.H., et al., 2011, "General properties of transcriptional time series in *Escherichia coli*", Nature Genetics, vol. 43, No. 6, pp. 554-560.*
Hilfinger, A, et al., 2011, "Separating intrinsic from extrinsic fluctuations in dynamic biological systems", Proceedings of the National Academy of Sciences, U.S.A., vol. 108, No. 29, pp. 12167-12172.*
Feng, H., et al., 2012, "Landscape and global stability of non-adiabatic and adiabatic oscillations in a gene network", Biophysical. Journal, vol. 102, pp. 1001-1010.*
Feng, H., et al., 2012, "Analytical calculation of protein production distributions in models of clustered protein expression", Physical Review E: Statistical, Nonlinear, and Soft Matter Physics, vol. 85, No. (3-1), pp. 031904/1-031904/9.*
Hensel, Z., et al., 2012, "Stochastic expression dynamics of a transcription factor revealed by single-molecule noise analysis", Nature Structural & Molecular Biology, vol. 19, No. 8, pp. 797-802.*
Hensel, Z., et al., 2013, "Single-molecule methods for studying gene regulation in vivo", Pfluegers Archiv—European Journal of Physiology, vol. 465, No. 3, pp. 383-395.*
Hensel, Z., et al., 2013, "Single-molecule imaging of gene regulation in vivo using cotranslational activation by cleavage (CoTrAC)" Journal of Visualized Experiments, No. 73, e50042, doi:10.3791/50042 (text abstract of video recording).*
Hensel, Z., et al., 2013, "Transcription-factor-mediated DNA looping probed by high-resolution, single-molecule imaging in live *E. coli* cells", PLoS Biology, vol. 11, No. 6, e1001591 (17 pages).*
Austin, D., et al., (2006) "Gene network shaping of inherent noise spectra", Nature, vol. 329, pp. 608-611.
Bailone, A., et al., (1979) "Inactivation of Prophage A Repressor in Vivo", J. Mol. Biol., vol. 131, pp. 553-572.
Bar-Even, A., et al., (2006) "Noise in protein expression scales with natural protein abundance", Nature Genetics, vol. 38, No. 6, pp. 636-643.
Blake, W., et al., (2006) "Phenotypic Consequences of Promoter-Mediated Transcriptional Noise", Molecular Cell, vol. 24, pp. 853-865.
Cai, L., et al., (2006) "Stochastic protein expression in individual cells at the single molecule level", Nature, vol. 440, pp. 358-362.
Choi, P.J., et al., (2010) "A stochastic single-molecule event triggers phenotype switching of a bacterial cell", NIH-PA Author Manuscript, Science, vol. 322, pp. 1-12.
Chubb, J.R., et al., (2006) "Transcriptional Pulsing of a Developmental Gene", Current Biology, vol. 16, pp. 1018-1025.

(Continued)

*Primary Examiner* — Kagnew H Gebreyesus
(74) *Attorney, Agent, or Firm* — Johns Hopkins Technology Ventures

(57) ABSTRACT

A method for measuring expression of autoregulatory molecules within living cells is provided. An autoregulatory molecule and marker construct is expressed in vivo, where the marker is cleaved from the construct during translation. The method comprises the expression of a construct having an autoregulatory molecule bound to a measurable expression marker by a cleavable linker. The cleavable linker is the substrate of a protease, which acts on its substrate in vivo during translation. Cleavage during translation, allows the autoregulatory molecule to fold normally as it would in its native form. The measurable marker is released and available for detection upon cleavage by the protease. As a result, the concentration of the measurable marker is directly related to the level of expression of the autoregulatory molecule.

6 Claims, 20 Drawing Sheets

(56) References Cited

PUBLICATIONS

Chubb, J.R., et al., (2010) "Bursts and pulses: Insights from single cell studies into transcriptional mechanisms", Current Opinion in Genetics & Development, vol. 20, pp. 478-484.
Datsenko, K.A. et al., (2006) "One-step inactivation of chromosomal genes in *Escherichia coli* K-12 using PCR products", PNAS, vol. 97, pp. 6640-6645.
Elowitz, M.B., et al., (2002) "Stochastic Gene Expression in a Single Cell", Science, vol. 297, pp. 1183-1192.
Feng, H., et al., (2011) "Adiabatic and Non-Adiabatic Non-Equilibrium Stochastic Dynamics of Single Regulating Genes", The Journal of Physical Chemistry B, vol. 115, pp. 1254-1261.
Haidong, F., et al., (2011) "A new formulation of two-time correlation functions of Markov chains applied to gene networks", Chemical Physics Letters, vol. 501, pp. 562-566.
Gillespie, D.T., (1977) "Exact Stochastic Simulation of Coupled Chemical Reactions", The Journal of Physical Chemistry, vol. 81, pp. 2340-2361.
Hawley, D.K., (1982) "Mechanism of Activation of Transcription Initiation from the λ Prm Promoter", J. Mol. Biol., vol. 157, pp. 493-525.
Hawley, D.K., et al., (1983) "The Effect of a Lambda Repressor Mutation on the Activation of Transcription Initiation from the Lambda λ Prm Promoter", Cell., vol. 32, pp. 327-333.
Hornos, J.E.M., et al., (2005) "Self-Regulating Gene: An Exact Solution", Physical Review E, vol. 72, pp. 051907-1-051907-5.
Huh, D., et al. (2011) "Non-genetic heterogeneity from stochastic partitioning at cell division", Nature Genetics, vol. 43, pp. 95-102.
Kalmar, T., et al., (2009) "Regulated Fluctuations in Nanog Expression Mediate Cell Fate Decisions in Embryonic Stem Cells", PLoS Biology, vol. 7, pp. 1-16.
Kielbasa, S.M., et al., (2008) "Transcriptional Autoregulatory Loops Are Highly Conserved in Vertebrate Evolution", PLoS ONE, vol. 3, pp. 1-7.
Lepzelter, D., et al. (2007) "Dynamics and Intrinsic Statistical Fluctuations of a Gene Switch", J. Phys. Chem. B., vol. 111, pp. 10239-10247.
Levine, A., et al., (1979) "Cellular Levels of the Prophage λ and 434 Repressors", J. Mol. Biol., vol. 131, pp. 655-661.
Little, J.W., et al., (1999) "Robustness of a Gene Regulatory Circuit", The EMBO Journal, vol. 18, pp. 4299-4307.
Lu, T., et al., (2006) "Effective Temperature in Stochastic Kinetics and Gene Networks", Biophysical Journal, vol. 91, pp. 84-94.
Meyer, B.J., (1980) "Gene Regulation at the Right Operator (0r) of Bacteriophag λ", J. Mol. Biol., vol. 139, pp. 163-194.
Nickels, B.E., et al., (2002) Protein-Protein and Protein-DNA Interactions of o70 Region 4 Involved in Transcription Activation by λcI, J. Mol. Biol., vol. 324, pp. 17-34.
O' Sullivan, J.M., et al., (2004) "Gene loops juxtapose promoters and terminators in yeast", Nature Genetics, vol. 36, pp. 1014-1018.
Pedraza, J.M., et al., (2005) "Noise Propagation in Gene Networks", Science, vol. 307, pp. 1965-1969.
Pedraza, J.M., et al., (2008) "Effects of Molecular Memory and Bursting on Fluctuations in Gene Expression", Science, vol. 319, pp. 339-343.
Raj, A, et al., (2006) "Stochastic mRNA Synthesis in Mammalian Cells", PLoS Biology, vol. 4, pp. 1707-1719.
Raser, J.M. et al., (2004) "Control of Stochasticity in Eukaryotic Gene Expression", Science, vol. 304, pp. 1-9.
Reichardt, L. et al., (1971) "Control of λ Repressor Snythesis", Proc. Nat. Acad. Sci. USA, vol. 68, pp. 2185-2189.
Rosenfeld, N., et al., (2005) "Gene Regulation at the Single-Cell Level", Science, vol. 307, pp. 1962-1965.
Sarai, A., et al., (1989) "λ Repressor Recognizes the Approximately 2-fold Symmetric Half-Operator Sequences Asymmetrically", Proc. Natl. Acad., Sci., vol. 86, pp. 6513-6517.
Shahrezaei, V., et al., (2008) "Analytical distributions for stochastic gene expression", Proc. Natl. Acad. Sci., vol. 105, pp. 17256-17261.
Shen-Orr, S.S., et al., (2002) "Network motifs in the transcriptional regulation network of *Escherichia coli*", Nature Genetics, vol. 31, pp. 64-68.
Simpson, M.L., et al., (2003) "Frequency domain analysis of noise in autoregulated gene circuits", Pro. Natl. Acad. Sci., vol. 100, pp. 4551-4556.
Singh, A., et al., (2009) "Stochastic Gene Expression As a Molecular Switch for Viral Latency", Current Opinion in Microbiology, vol. 12, pp. 460-466.
Suter, D., et al., (2011) "Mammalian Genes Are Transcribed with Widely Different Bursting Kinetics", Science, vol. 332, pp. 472-474.
Sutherland, H., et al. (2009) "Transcription Factories: Gene Expression in Unions?", Nature Reviews, vol. 10, pp. 457-466.
Swain, P.S., et al., (2002) "Intrinsic and Extrinsic Contributions to Stochasticity in Gene Expression", Proc. Natl. Acad. Sci., vol. 99, pp. 12795-12800.
Tao, Y., et al., (2007), "Effect of Feedback Regulation on Stochastic Gene Expression", Journal of Theoretical Biology, vol. 247, pp. 827-836.
Tobias, J.W., et al., (1991) "The N-End Rule in Bacteria", Science, vol. 254, pp. 1374-1377.
Tobias, J.W., et al. (1991) "Cloning and Functional Analysis of the Ubiquitin-Specific Protease Gene UBP1 of *Saccharomyces cerevisiae*", The Journal of Biological Chemistry, vol. 266, pp. 12021-12028.
Wang, J., (2003) "Statistics, pathways and dynamics of single molecule protein folding", Journal of Chemical Physics, vol. 118, pp. 952-958.
Wang, J., et al., (1995) "Intermittency of Single Molecule Reaction Dynamics in Fluctuating Environments", Physical Review Letters, vol. 74, pp. 4317-4320.
Weigle, J.J.,et al., (1951) "Mutual Exclusion Between an Infecting Phage and a Carried Phage", California Institute of Technology, vol. 62, pp. 301-318.
Zenklusen, D., et al., (2008) "Single-RNA Counting Reveals Alternative Modes of Gene Expression in Yeast", Natl. Struct. Mol. Biol., vol. 15, pp. 1263-1271.
Zong C., et al., (2010) "Lysogen Stability is Determined by the Frequency of Activity Bursts from the Fate-Determining Gene", Molecular Systems Biology, vol. 6, pp. 1-12.

\* cited by examiner

CO-TRANSLATIONAL ACTIVATION OF A TRANSCRIPTION FACTOR BY PROTEOLYTIC CLEAVAGE AND METHODS OF USE

CROSS REFERENCE TO RELATED APPLICATION

This application is based upon and claims priority from U.S. Provisional Patent Application Ser. No. 61/840,891 entitled "CO-TRANSLATIONAL ACTIVATION OF A TRANSCRIPTION FACTOR BY PROTEOLYTIC CLEAVAGE AND METHODS OF USE" filed with the U.S. Patent and Trademark Office on Jun. 28, 2013, by the inventors herein, the specification of which is incorporated herein by reference.

STATEMENT OF GOVERNMENTAL INTEREST

This invention was made with government support under grant no. MCB-0746796, awarded by the National Science Foundation. The government has certain rights in the invention.

BACKGROUND OF THE INVENTION

Field of the Invention

This invention relates to the field of biotechnology and, more specifically, to methods of measuring biological function of molecules in vivo.

DESCRIPTION OF THE BACKROUND

Transcription factors (TFs) play important roles in gene regulation and cell fate determination. Many TFs are expressed at low levels[1]. Intrinsic stochasticity in TF expression inevitably influences gene regulation[2,3]. Approximately half of *E. coli* TFs regulate their own expression through autoregulatory feedback loops[4], suggesting that autoregulation may counter intrinsic stochasticity. More specifically, CI in *E. coli* autoregulates its own expression through coupled positive and negative feedback. It is responsible for maintaining an extremely stable lysogenic state and also the rapid switching to lytic growth under induction. Fluctuations in CI concentrations affect such fate determination of a λ lysogen. Intrinsic stochasticity in CI expression is largely influenced by its expression level, irrespective of positive or negative autoregulation. Furthermore, global, cell-to-cell variation, or extrinsic noise, is primarily responsible for fluctuations in CI concentration, with intrinsic noise playing a relatively small role.

Measurements of the stochastic expression dynamics of TFs can provide important insight into how TFs influence the precision and robustness of gene regulation. However, it has been difficult to probe TF expression in real time at the single-molecule level. Previously, the production of single protein molecules in live *E. coli* cells was detected by fusing a fast-maturing fluorescent protein, Venus, to a membrane-targeting sequence, Tsr[5]. Such method is not suitable for probing the stochastic expression of TFs because fusing Tsr-Venus to a TF will likely disrupt DNA binding, oligomerization or other essential functions.

SUMMARY OF THE INVENTION

One embodiment of the present invention provides a method for measuring expression of an autoregulatory molecule. In one step of the method, a construct for expression of an autoregulatory molecule is introduced in a cell for expression. The construct comprises the autoregulatory molecule, a measurable marker, and a cleavable substrate in a single molecule. In another step of the method, a protease capable of cleaving the cleavable substrate in the cell is expressed. In a subsequent step, the protease cleaves the cleavable substrate during translation allowing the autoregulatory molecule to fold into a functional molecule. In yet a further step, the presence of the measurable substrate is evaluated.

A further embodiment of the present invention provides a purified and isolated polynucleotide encoding the construct to be used in the method described above. The polynucleotide has a sequence that encodes an autoregulatory molecule, a measurable marker, and a cleavable substrate. The polynucleotide sequence encoding the cleavable substrate connects the polynucleotide sequence encoding the autoregulatory molecule and the polynucleotide sequence encoding the measurable marker. The cleavable substrate is capable of being cleaved during translation of the polynucleotide. When expressed in a cell, the cleavable substrate is cleaved by a protease releasing the measurable marker and allowing the autoregulatory molecule to fold functionally. The measurable marker is also released and capable of being measured by standard techniques.

BRIEF DESCRIPTION OF THE DRAWINGS

The above and other features, aspects, and advantages of the present invention are considered in more detail, in relation to the following description of embodiments thereof shown in the accompanying drawings, in which:

FIG. 1(*b*) is a Western blot examining cleavage efficiency under an elevated expression level of the $\lambda^{wt}$ construct on a multi-copy plasmid. Lanes 1 and 2: anti-Venus blot in the absence and presence of Ubp1. The intensity of the Tsr-Venus-Ub band (100 kD, lane 2) is much higher than that of the full-length Tsr-Venus-Ub-CI band (127 kD, lane 1), indicating that CI is activated to enhance its own expression by the removal of the N-terminal Tsr-Venus-Ub fusion. Lanes 4-5: Anti-CI blot in the absence and presence of Ubp1. CI is found at its wild-type molecular weight (27 kD) upon Ubp1 cleavage. Lane 3 is the anti-CI blot of a negative control strain DH5α, which does not harbor the $\lambda^{wt}$ construct plasmid.

FIG. 2(*b*) shows brightfield and fluorescence images of a $\lambda^{r3}$ colony showing how CI expression is tracked in single cell lineages (such as the one outlined).

FIG. 2(*c*) is a time trace of CI production in single cell lineages for each strain. Plots show the number of CI molecules produced in 5-min. intervals, starting from the first cell division. Red dashed lines indicate cell division.

DETAILED DESCRIPTION OF THE INVENTION

Figure 1A:
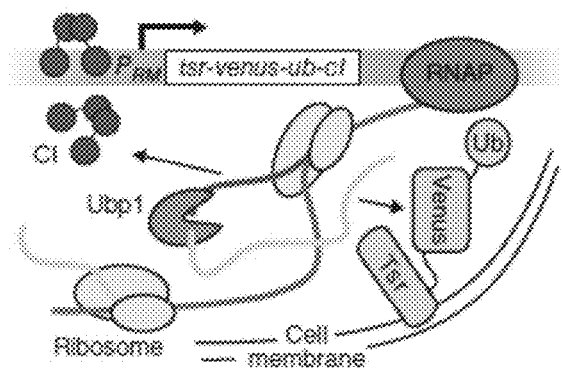
FIG. 1(*a*) is a schematic drawing of the CoTrAC strategy. The membrane-targeted reporter Tsr-Venus-Ub is expressed in translational fusion with λ repressor CI. A protease, Ubp1, co-translationally cleaves the nascent Tsr-Venus-Ub-CI polypeptide, separating the reporter from CI. The fluorescent reporter is then detected individually on the cell membrane, while CI binds to DNA to regulate its own transcription.

The invention summarized above may be better understood by referring to the following description. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Targeted activation of a protein molecule of interest in a living cell is accomplished through the method described herein. In one embodiment, a molecule of interest is expressed with its N-terminus fused to a coding sequence. Many naturally expressed peptide molecules are inactive when fused to other molecules, whether amino acids, nucleotides, or other peptides. In many instances, inactivation occurs when fusion occurs at the peptide molecule's N-terminus because such a fusion inhibits proper folding of the peptide during translation. Surprisingly, however, if the naturally expressed peptide is fused to another molecule having a sequence that can be recognized by a protease capable of cleaving the second molecule during translation, it is possible for the naturally expressed peptide to fold correctly and function in the cell. When the protease is co-expressed with the fused peptide and specifically separates the molecule of interest from the fusion sequence, the molecule then exists in its native form and can function properly. Additionally, the expression of each molecule of interests corresponds to the expression of a single fusion molecule; this can be exploited to directly count the expression of molecules without affecting their function if the fusion sequence includes a measurable marker, such as a fluorescent protein.

In one embodiment, a method for measuring expression of an autoregulatory molecule is provided. The first step of the method is to express a fusion construct in a cell. The fusion construct is a molecule of interest that serves a particular function in the cell. In one example, the molecule of interest is an autoregulatory molecule, such as CI in *E. coli* as shown in the examples. However, a person of ordinary skill in the art would recognize that other molecules that require native folding for controlled expression could be utilized. It is contemplated that transcription factor CI can be replaced with other transcription factors or enzymes as the molecule of interest.

The fusion construct further includes a cleavable substrate. In some embodiments the cleavable substrate is recognized by an endogenous protease, where the endogenous protease can be controlled. In other embodiments the cleavable substrate is recognized by an exogenous protease, which has been engineered to be expressed in the cell under specific conditions. In one example, as shown below, the exogenous protease is expressed in a plasmid where expression can be induced. In some preferred embodiments, the cleavable sequence is the sequence of ubiquitin, which is cleaved by deubiquitinase when both are co-expressed in a host cell. This method can be applied to eukaryotic organisms if the ubiquitin sequence is replaced with a sequence that would not be recognized by native proteases (e.g. PreScission Protease or other proteases that do not leave any/many extra amino acid residues at the C-terminal end of a cleavage site).

A third component of the fusion construct is a measurable marker, which is released during translation of the construct by cleavage of the cleavable substrate by the protease. The measurable marker, as recognized in the art may include any type of known marker which can be detected by various means. Such markers may include fluorescent peptides, colorimetric compounds, chemiluminescent peptides, and other measurable markers. Fluorescent markers may include yellow fluorescent protein (YFP), blue fluorescent protein (BFP), green fluorescent protein (GFP), red fluorescent protein (RFP) and fluorescing mutants thereof. In a preferred embodiment YFP Venus is used as the marker. Colorimetric compounds may include of glutathione-S-transferase (GST), beta-galactosidase (B-gal), and alkaline phosphatase.

In another embodiment, a purified and isolated polynucleotide that encodes the construct described above is provided. The purified and isolated polynucleotide can be obtained by recombinant methods known in the art as described in the examples below. The purified and isolated polynucleotide can then be included in an expression vector to be introduced into cells capable of expressing the vector. In other embodiments, the polynucleotide can be introduced in cells by recombinant methods known in the art. The purified polynucleotide can be expressed in cells in which expression of the protease can be induced. In other embodiments, the polynucleotide is expressed in cells with an exogenous protease vector that can be inducibly expressed.

In yet further embodiments, different reporter constructs can be used to track multiple different types of molecules in one cell, this method is also applicable to counting the simultaneous expression of two or more types of molecules (limited only by the diversity of reporter molecules, different fluorescent protein colors, etc). A person of ordinary skill in the relevant art would understand that multiple constructs can be co-expressed in the cells in order to measure each separate marker.

EXAMPLES

Using the novel, single-molecule strategy described above as Co-Translational Activation by Cleavage (CoTrAC), we probed the effect of autoregulation on the stochastic expression dynamics of a fate-determining TF, the bacteriophage λ repressor CI, in live *E. coli* cells.

In the CoTrAC strategy, we translationally fused Tsr-Venus to CI with the yeast ubiquitin (Ub) sequence inserted in between. The deubiquitinase Ubp1 was co-expressed to co-translationally cleave the emergent polypeptide after the C-terminal Ub residue'. Once cleaved from Tsr-Venus-Ub, CI can bind DNA and regulate its own expression. At the same time, we measured the number of CI molecules expressed in real time by counting Tsr-Venus-Ub reporter molecules on the membrane; translational fusion ensured that for each CI molecule one reporter molecule was produced. We note that transcriptional fusion, in which Tsr-Venus and Clare expressed from separate ribosome binding sites (RBS) on the same mRNA, is not accurate due to variations in the number of protein molecules produced from identical mRNA molecules[5]. Measuring the absolute number of molecules in real time instead of using arbitrary fluorescent units is critical in analyzing the underlying stochastic gene expression mechanisms[8].

Figure 1B:
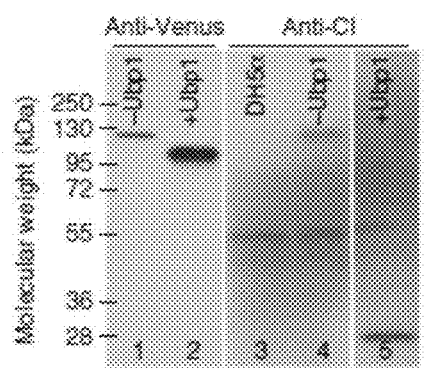
Figure 5A:
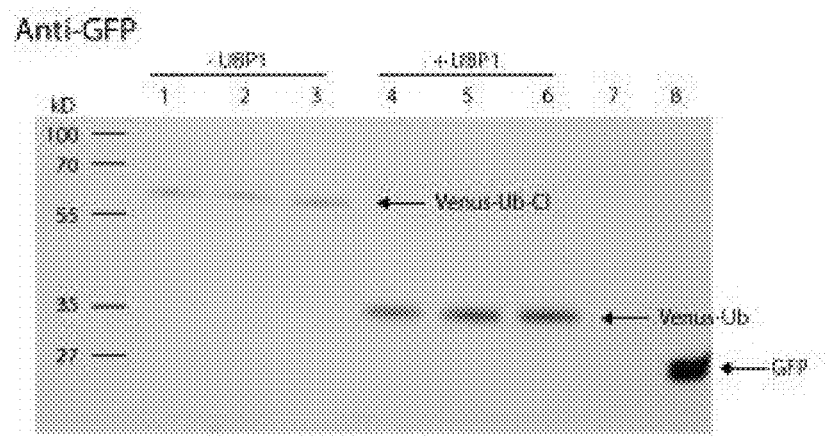
FIG. 5(a) is an anti-GFP Western blot used to quantify the molar ratio between separated Venus-Ub and CI. Cells harboring plasmid pZH051t that expresses Venus-Ub-CI in the absence (lanes 1-3) or presence lanes 4-6) of Ubp1 were loaded on two identical gels in triplicate. Tsr was eliminated in plasmid pZH051t to avoid uneven transfer from the polyacrylamide gel to nitrocellulose membrane (Venus-Ub and CI have similar molecular weights of 35 and 27 kD, respectively). Lane 7 is the negative control strain DH5α, which does not harbor pZH51t, and lane 8 is loaded with 1 ng purified GFP. The molar ratio of Venus:CI after cleavage is calculated by comparing the ratios of the intensities of the uncleaved and cleaved bands is normalized to the uncleaved band on the corresponding blot. Each sample is loaded three times and the experiment was repeated in triplicate with independent samples; the averaged Venus:CI ratio is calculated at 1.1±0.1.
Figure 5B:
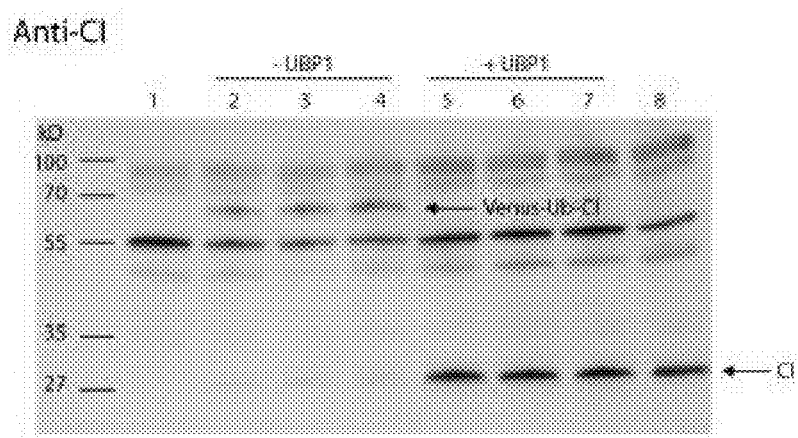
FIG. 5(b) is an anti-CI Western blot used to quantify the molar ratio between separated Venus-Ub and CI. Cells harboring plasmid pZH051t that expresses Venus-Ub-CI in the absence lanes 2-4) or presence (lanes 5-7) of Ubp1 were loaded on two identical gels in triplicate. Tsr was eliminated in plasmid pZH051t to avoid uneven transfer from the polyacrylamide gel to nitrocellulose membrane (Venus-Ub and CI have similar molecular weights of 35 and 27 kD, respectively). Lane 1 is the negative control strain DH5α and lane 8 is the positive control strain JL5932, a wild-type λ lysogen. The molar ratio of Venus:CI after cleavage is calculated by comparing the ratios of the intensities of the uncleaved and cleaved bands is normalized to the uncleaved band on the corresponding blot. Each sample is loaded three times and the experiment was repeated in triplicate with independent samples; the averaged Venus:CI ratio is calculated at 1.1±0.1.

Using immunoblotting, we verified that cleavage between the Ub and CI sequences of Tsr-Venus-Ub-CI is complete, even at expression levels much higher than those in a λ lysogen. We observed no significant accumulation of uncleaved fusion protein when it is expressed from a multicopy plasmid under the control of CI's native promoter $P_{RM}$ (FIG. 1(b), lane 2). In addition, CI was expressed at a higher level in the presence of Ubp1 than in its absence, indicating that CI activates its own expression once cleaved from Tsr-Venus-Ub (FIG. 1b, lanes 1 and 2, 4 and 5). Finally, the calculated molar ratio of Tsr-Venus-Ub to CI molecules was 1.1±0.1, consistent with equal production of Tsr-Venus-Ub and CI (FIGS. 5a-b). Based on these observations, we conclude that the CoTrAC strategy is well suited for probing the expression dynamics of a TF accurately in real time and at the single-molecule level.

Stochastic Expression of CI

Figure 6A:
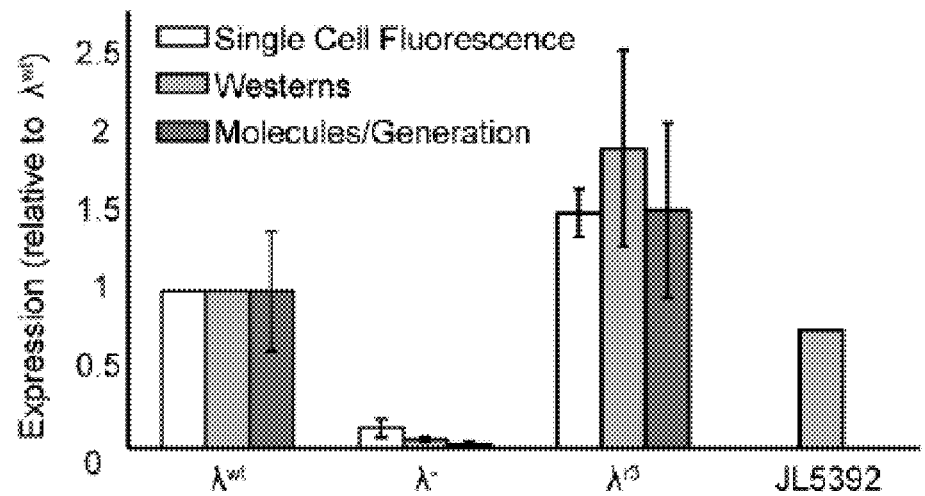
FIG. 6(a) is a comparison of CI expression levels in $\lambda^{wt}$, $\lambda^{1}$ and $\lambda^{b}$ measured by three different methods: single-cell fluorescence acquired by steady-state fluorescence microscopy, Westerns by immunoblotting against YFP and/or CI, and molecules/generation calculated from time-lapse fluorescence microscopy. The CI expression levels in strains $\lambda^{-}$ and $\lambda^{r3}$ were normalized to that of $\lambda^{wt}$ measured in each method. The resulting relative expression levels of CI measured using the three different methods are indistinguishable from each other within error. The lysogen strain JL5392 was only measured using immunoblotting against CI as shown in B. Error bars show standard deviation.
Figure 6B:
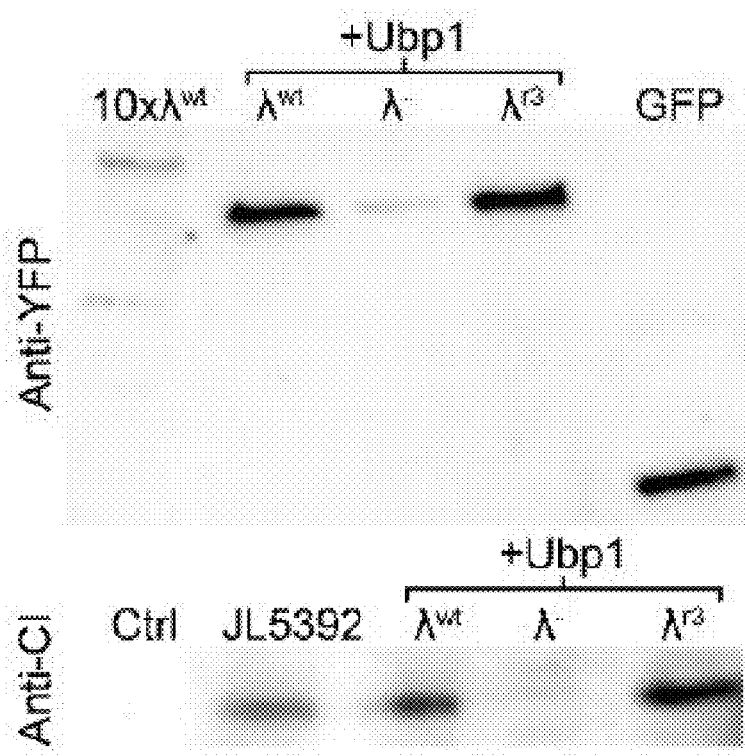
FIG. 6(b) is a typical immunoblot used to generate the Western data in 6(a). In the anti-YFP blot, the $\lambda^{wt}$ strain lacking Ubp1 expression is loaded in 10-fold excess in order to be visible on the blot. The uncleaved Tsr-Venus-Ub-CI band is still much dimmer than the bands for $\lambda^{wt}$ and $\lambda^{r3}$, indicating that the removal of the Tsr-Venus-Ub reporter from the N-terminus of CI activates CI to enhance its own expression. The anti-CI blot (quantified in 6(a)) shows that a wild-type λ lysogen, JL5392, has a similar CI expression level to $\lambda^{wt}$.

We used the CoTrAC strategy to study the stochastic expression of CI, aiming to find out what roles different regulatory contexts play in minimizing the intrinsic stochasticity in CI expression. We constructed four strains, $\lambda^{wt}$, $\lambda^{r3}$, $\lambda^b$ and $\lambda^-$ (FIG. 2a, Table S1), by replacing cI-rexA-rexB in the immunity region of phage λ with tsr-venus-ub-cI and incorporating this region (cro through $O_L$) into the chromosome of *E. coli* strain MG1655. We constitutively expressed the protease Ubp1 from a plasmid when appropriate. In $\lambda^{wt}$, all known regulatory elements relevant to λ lysogeny are retained; CI regulates its own expression through coupled positive and negative autoregulation. In $\lambda^{r3}$, a mutant $O_R$3-r3 operator effectively abolishes CI binding[9,10]; CI activates but does not repress its own expression. In $\lambda^b$, CI is constitutively expressed from $P_{RM}$ without autoregulation. In $\lambda^-$, Cro represses CI expression. Using fluorescence and immunobloting assays we verified that $\lambda^{wt}$ expresses CI at a level similar to that of a λ lysogen under the same growth conditions, and that the other three strains express CI at levels consistent with their modified regulatory contexts (FIGS. 6a-b). Thus, although our reporter $P_{RM}$-tsr-venus-ub-cI transcript and the lysogenic $P_{RM}$-cI-rexA-rexB transcript differ in sequence, the resulting CI expression levels are within the concentration range that is relevant to the autoregulation of $P_{RM}$ by CI.

Figure 2A:
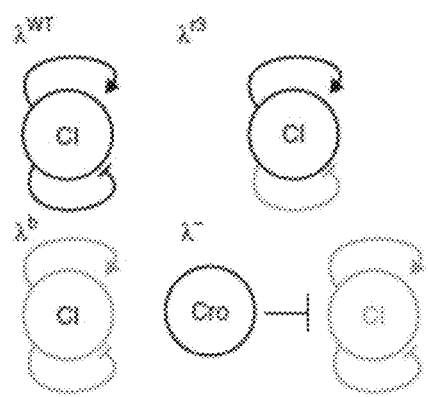
FIG. 2(*a*) shows regulation of the four strains used in the study. In $\lambda^{wt}$ CI both positively (indicated by curved arrow) and negatively (indicated by curve bar-end) autoregulates its own expression. In $\lambda^{r3}$ the negative autoregulation is disabled by mutating the $O_R3$ site (the curved arrow is grayed). In $\lambda^b$ both positive and negative autoregulation are disabled. In $\lambda^-$ CI expression (grayed) is repressed by Cro.
FIG. 2(d) shows histograms of number of CI molecules produced in 5-min frames for $\lambda^{wt}$, $\lambda^{r3}$ and $\lambda^{b}$. Histogram of $\lambda^{-}$ is shown in inset due to its significantly lower expression level.
Figure 2B:
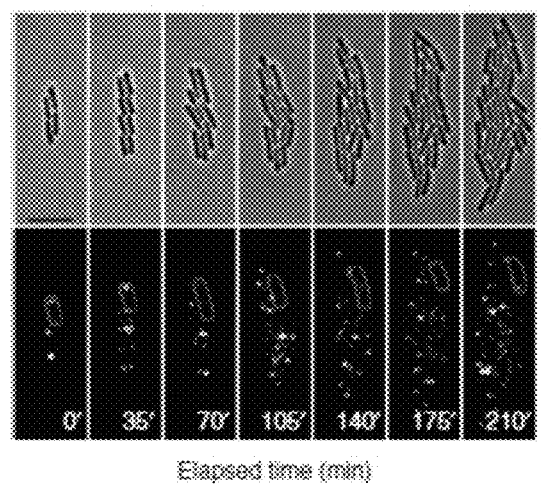
Figure 2C:
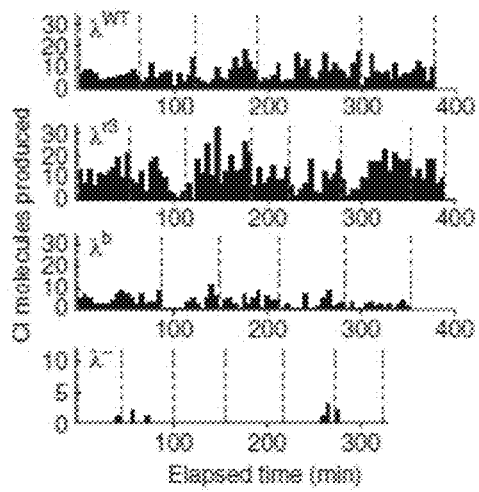

Next, we monitored CI expression dynamics in real time. We grew *E. coli* cells on a microscope stage for several generations and followed CI expression by counting the numbers of Tsr-Venus-Ub molecules produced in single cells (FIG. 2b). At five-minute intervals, we counted and then photobleached Tsr-Venus-Ub molecules so that only newly expressed fluorescent molecules would be counted in each measurement. Representative expression time traces for each strain are shown in FIG. 2c. In accordance with the bulk expression level measurements, we found that on average $\lambda^{wt}$ expressed 100±40 CI molecules per cell generation (resulting an average of ~140 CI molecules per cell in a steady-state culture), within the range of reported values of other studies[11,12].

Figure 2D:
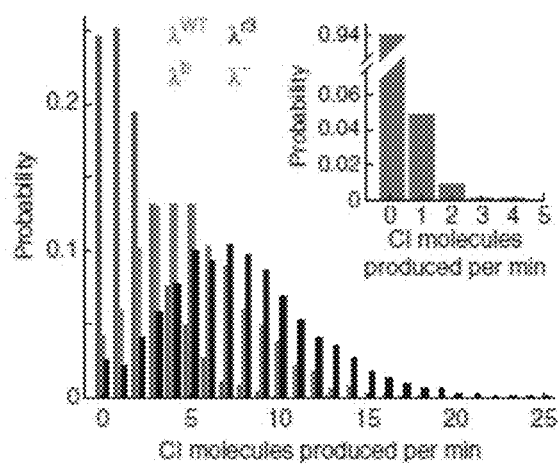

For all four strains, we found that CI expression time traces exhibited large fluctuations. For example, CI production in each 5-min. frame in $\lambda^{r3}$ varied from 0-43 CI molecules and fluctuated ~60% around its mean (7.8±4.4 CI molecules, corrected for cell cycle dependence, Supplementary Information). Table 1 lists the mean CI production rate per 5-min. and the corresponding noise (variance-mean-squared ratio, $\eta^2=\sigma^2/\mu^{2\ [13]}$) for all strains. Histograms of CI production in all 5-min. frames are shown in FIG. 2d. Note that distributions of protein production differ from steady-state protein concentration distributions—production distributions are time-dependent, allowing for a more complete characterization of the system by isolating its constituents based on time scale differences (see below).

To compare the stochasticity in CI production at different expression levels, we calculated the Fano factor, which normalizes the variance by the mean and is indicative of a system's stochasticity[14]. For all four strains, the Fano factors were greater than one (Table 1), consistent with the presence of noise stronger than that of a random, Poisson process[5,15]. We note that we monitored protein production instead of concentration, avoiding noise introduced by protein degradation[8] and random partitioning at cell division[16].

Figure 12:
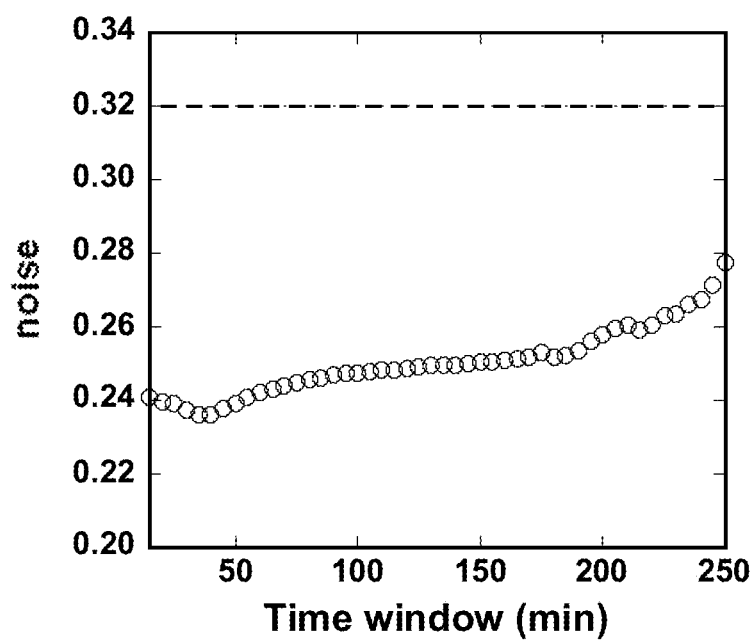
FIG. 12 is a time scale of extrinsic noise. The noise at each time window was calculated as the average of noise of all possible time window positions along a long CI production time trace of $\lambda^{r3}$. The averaged noise from all time traces (circles) at each time window is then plotted against the length of each time window. The population noise level of 0.32 is plotted as a dashed line.

Our real-time experiments made it possible to obtain both the overall noise in CI production from the whole population and the time scale of noise from individual time traces. For all four strains, CI production fluctuated rapidly from one 5-min. frame to the next. Previous work has shown that the global cellular environment does not change dramatically on such a short time scale, hence rapid fluctuations can be attributed to "intrinsic noise", which is an inevitable consequence of stochastic gene expression mechanisms—how individual mRNA and protein molecules are produced and degraded[3,14,17]. Additionally, we observed that fluctuations in CI production rates within individual lineages were smaller than those between cell lineages and slowly approached the population means at time scales much longer than one cell cycle (FIG. 12). This indicated the presence of slowly varying cell-to-cell heterogeneity, or extrinsic noise, due to global factors such as different numbers of RNA polymerase and ribosome molecules in different cells, as described in predominant models in stochastic gene expression studies[3,17,18]. The clear time scale separation between intrinsic and extrinsic noise has been observed previously[3].

Decomposition of Total Noise into Intrinsic Noise, Extrinsic Noise and Memory

The observation of both intrinsic and extrinsic noise indicated by the fast and slow fluctuations in CI production prompted us to develop a time-dependent noise analysis. This analysis made it possible to quantitatively decompose total noise into its constituents. We found that in addition to the aforementioned intrinsic and extrinsic noise, memory, or temporal correlations between individual expression events[8,19] also contributed to the total noise. The total noise, $\eta_{Nt}^2$, in the total number of CI molecules produced in N consecutive measurements up to one cell generation (t is the time between measurements, which is 5 min. in our experiment), can be expressed as the sum of intrinsic noise $\eta_{Nt,int}^2$, extrinsic noise $\eta_{ext}^2$, and noise resulting from memory C"(Nt):

$$\eta_{Nt}^2 = \frac{\sigma_{Nt}^2}{\langle n \rangle_{Nt}^2} = \eta_{Nt,int}^2 + \eta_{ext}^2 + C''(Nt) \quad (1)$$

Here we approximate extrinsic noise as a constant on the time scale of a single cell generation because of its long time scale in our experiments (FIG. 12). The memory term refers to noise that is temporally correlated on timescales short enough to be measured in single-generation time traces.

Next, we show that the autocorrelation of CI expression time traces at different time lags $\tau=t, 2t, \ldots Nt$, up to one cell generation time can be decomposed into two terms:

$$C(\tau) = \sigma_{ext}^2 + C'(\tau) \quad (2)$$

The first term describes the contribution of a constant extrinsic noise on the time scale examined (~one cell cycle). The second term, which describes the remaining autocorrelation, is related to the memory term C"(Nt) in Eq. 1 by $$C''(Nt) = \frac{2[(N-1)C'(t) + (N-2)C'(2t) + \ldots + C'(Nt-t)]}{N^2 \langle n \rangle_t^2} \quad (3)$$

If a protein production process has little memory ($C'(\tau)=0$), C"(Nt) in Eq. 1 is also zero across all time windows. The total noise can then be expressed as the sum of and $\eta_{Nt,int}^2$ and $\eta_{ext}^2$:

$$\eta_{Nt}^2 = \eta_{Nt,int}^2 + \eta_{ext}^2 = \frac{1}{\langle n \rangle_{Nt}} \frac{\sigma_t^2 - \sigma_{ext}^2}{\langle n \rangle_t} + \frac{\sigma_{ext}^2}{\langle n \rangle_t^2} = \frac{A}{\langle n \rangle_{Nt}} + B \quad (4)$$

Here, A is the intrinsic Fano factor (note the subtraction of the extrinsic Fano factor $\sigma_{ext}^2/\langle n \rangle_t$), and B is the time-independent extrinsic noise.

We note that previous work divided noise in gene expression into two components, intrinsic and extrinsic noise[17,18]. The extrinsic noise in our analysis, similar to that described in earlier work, refers to fluctuations in CI expression rate that arise from cell-to-cell variations affecting many genes. Our analysis holds when such fluctuations are approximately constant on the time scale of a cell cycle. The intrinsic noise in our analysis, however, only refers to fast, random fluctuations in CI production, a result of the random birth and death of individual mRNA and protein molecules. In bacterial cells, these can be treated as random processes given that transcription and translation are generally faster than protein degradation, cell growth and our temporal resolution (5 min).

Temporal correlation between individual expression events that is visible on the time scale of one cell cycle, such as that exhibited in a two-state gene activation/inactivation model[20-23], or when the switching kinetics is non-random[8,17,24], is included in intrinsic noise in previous studies, but classified as memory in our analysis. We treat this type of fluctuation independently as memory because it originates from different molecular mechanisms such as the aforementioned gene activation/inactivation switching or TF binding/unbinding kinetics. These processes normally occur more slowly than the synthesis and degradation of individual mRNA or protein molecules in bacterial cells. Theoretical studies have shown that this type of fluctuation (often called non-adiabatic fluctuation) contributes significantly to total protein expression noise[25-28]. It may also play an important role in determining or maintaining a cell's fate due to its slower time scale than that of intrinsic noise from statistical fluctuations of molecular numbers, which can be "averaged out" over longer time scales[29-31]. Here, we provide a way to isolate and quantify memory based on the different time scale at which it operates relative to intrinsic and extrinsic noise. The presence and characteristics of memory can be readily determined from time-dependent measurements of protein production, either measured directly as in our experiments, or inferred from changes in protein concentrations[3]. We emphasize that regardless of the nomenclature of different components of noise, the time-dependent noise analysis is valid for any process in which noise can be separated into components acting on different timescales.

Noise Analysis of CI Production

Figure 3A:
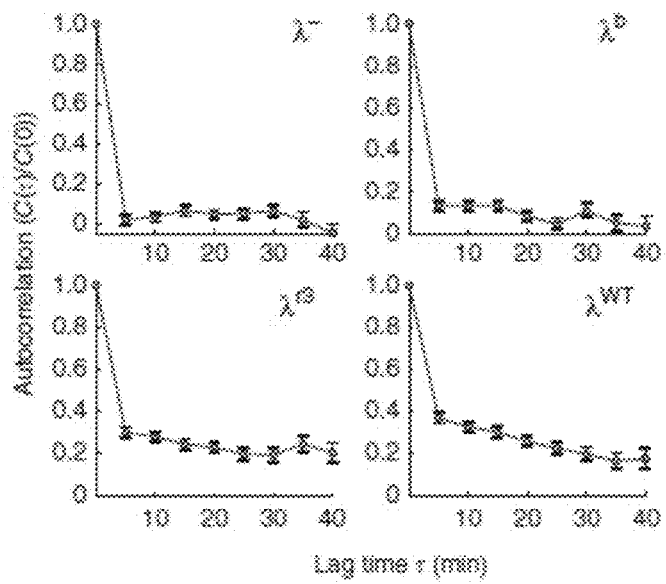
FIG. 3(a) shows normalized autocorrelation curves from single-generation time traces for the four strains. CI production autocorrelation in $\lambda^{r3}$, $\lambda^{b}$, and $\lambda^{-}$ is essentially flat at all time lags; autocorrelation in $\lambda^{wt}$ is highest at short time lag and decreases gradually. Autocorrelation of the four strains computed using long time traces of multiple generations showed similar trends (FIG. 13).
Figure 13:
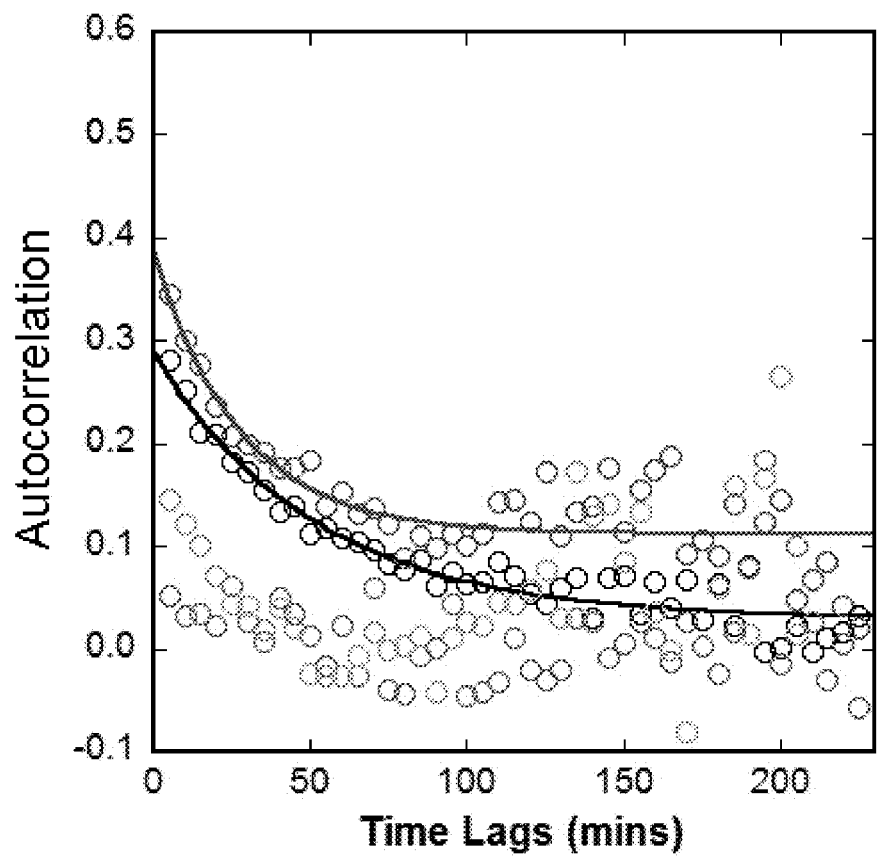
FIG. 13 shows autocorrelation of the four strains using long time traces spanning multiple cell generations. The solid curves are the single exponential fitting for $\lambda^{wt}$ and $\lambda^{R3}$ with an apparent decay half time at ~20 min and 50 min, respectively. Single exponential fitting to $\lambda^b$ and $\lambda^-$ results in poor fitting and large error bars possibly due to the low and autocorrelation values and large error ranges.

We used the time-dependent noise analysis to study noise in CI production. We first computed the autocorrelation of CI production time traces of single generations for all strains (FIG. 3a). For $\lambda^{r3}$, $\lambda^b$, and $\lambda^-$, the autocorrelation drops at the first 5-min. time lag, quickly reaching a non-zero plateau at longer time scales. The initial rapid drop of autocorrelation indicates the presence of fast, memoryless fluctuations, or intrinsic noise, in the CI production process. The non-zero plateau indicates slowly varying extrinsic noise—the value of the plateau is determined by the variance of the extrinsic noise (Eq. 2). In contrast, after the initial drop, the autocorrelation of $\lambda^{wt}$ gradually decays with relatively large values at short time lags, and finally flattens at long time lags. This behavior is characteristic of a process that has temporally correlated fluctuations, or memory, in addition to memoryless intrinsic noise and extrinsic noise that is constant on the scale of one cell cycle. The time at which the autocorrelation falls to half of that at the first time lag is ~20 min, suggesting that fluctuations in CI production only last a short portion of a cell cycle (~65 min). Autocorrelation computed from long CI expression time traces of multiple generations further confirmed these observations (FIG. 13). Note that protein concentration autocorrelation can be dominated by slow protein degradation[32,33], making it less suitable to examine memory in protein production. We did not observe significant correlation above a constant plateau despite positive autoregulation by CI for $\lambda^{r3}$ on the time scale of one cell cycle. This is reasonable as the operator sites $O_R1$ and $O_R2$ are almost saturated by CI at lysogenic CI concentrations[34], therefore $P_{RM}$ should almost always be in the activated state.

Figure 3B:
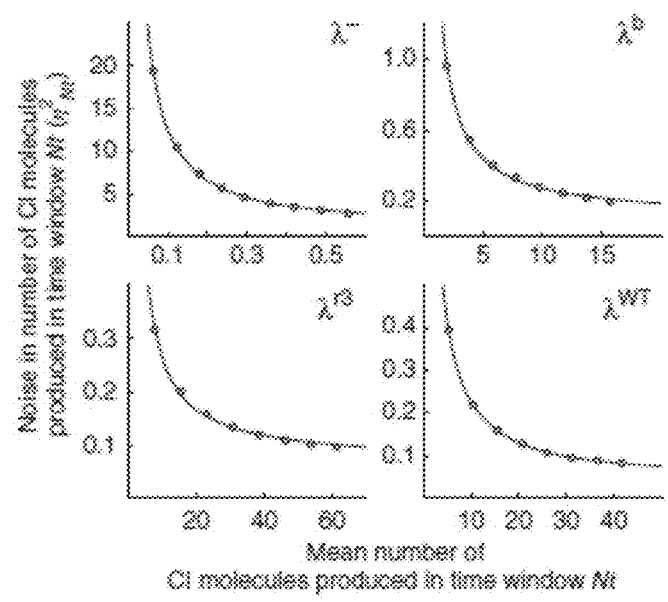
FIG. 3(b) shows noise curves fit to Eq. 4. Noise ($\sigma^2/\mu^2$) in $\lambda^{r3}$, $\lambda^{b}$, and $\lambda^{-}$ can be decomposed into the sum of intrinsic noise that scales inversely with the mean number of molecules (u) produced and a constant extrinsic noise; $\lambda^{wt}$ is well fit only after the subtraction of memory from total noise.

Given that CI production is nearly memoryless in $\lambda^{r3}$, $\lambda^b$ and $\lambda^-$ on the time scale of one cell cycle, the observed noise is simply the sum of intrinsic and extrinsic noise. We plotted the noise in the number of CI molecules produced in a given time window, $\eta_{Nt}^2$, as a function of the mean number of molecules, $\langle n \rangle_{Nt}$, produced in that time window (FIG. 3b). We found that the resulting noise curves were well fit by Eq. 4. In contrast, for $\lambda^{wt}$, the noise curve was well fit as the sum of intrinsic and extrinsic noise only after the memory effect was estimated from the autocorrelation and subtracted from the total noise (FIG. 14 a-c). Fitting results for the intrinsic Fano factor and extrinsic noise are listed in Table 1. The decomposition of the total noise in CI production into intrinsic noise, extrinsic noise and memory enabled us to examine how regulatory contexts influence these noise components and provided valuable insight into the underlying stochastic mechanism of CI production.

Effect of Regulatory Context on CI Expression Noise

Figure 4A:
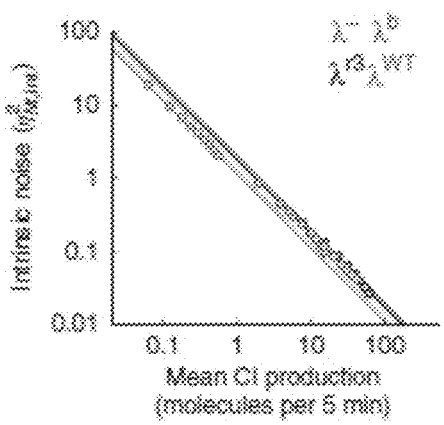
FIG. 4(a) shows intrinsic noise of the four strains is influenced largely by the mean CI production level—the close-to-three orders of magnitude change in the CI production level across the four strains results in a similar fold change of intrinsic noise, but less than two-fold change in the intrinsic Fano factors. The lines (y=A/x) are plotted in logarithmic scale using the fitted Intrinsic Fano Factors from FIG. 3(b) for each strain. The smaller axis intercept of the $\lambda^{-}$ line from that of the other three strains indicates a smaller intrinsic Fano Factor for $\lambda^{-}$.

Comparing the noise properties of the four strains, we found that in contrast with our previous expectation, intrinsic noise is mainly influenced by the average expression level and that different regulatory contexts have little direct impact on this property. FIG. 4a shows that regardless of the presence or absence of positive and negative autoregulation, intrinsic noise scales inversely with the expression level in $\lambda^b$, $\lambda^{wt}$ and $\lambda^{r3}$. Similar dependence of intrinsic noise on mRNA or protein expression levels has also been observed previously in yeast and E. coli[1,21,35]. Hence, a growing body of evidence has shown that the magnitude of intrinsic noise in gene expression is largely independent of different organisms, promoters, growth conditions and regulatory contexts but instead is determined by expression levels, suggesting common transcriptional and translational mechanisms in stochastic gene expression.

Figure 4B:
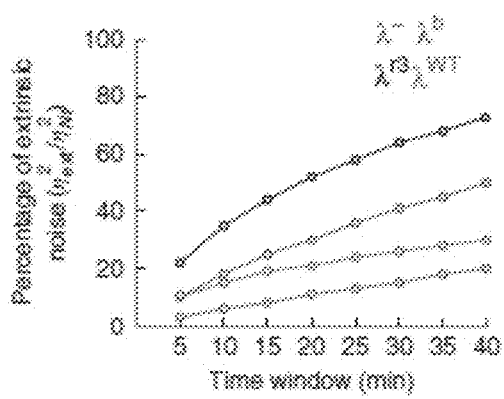
FIG. 4(b) shows extrinsic noise as a fraction of total noise in total CI production in a given time window. Extrinsic noise accounts for a significant fraction of total noise at the shortest time window at relatively high expression levels, and is significant in all strains at timescales approaching one cell cycle.

Next, we analyzed the extrinsic noise levels in the four strains. We found that at extremely low expression levels (<1 molecule per cell cycle.) such as in $\lambda^-$, intrinsic noise dominates; at moderate expression levels such as in $\lambda^b$, $\lambda^{wt}$ and $\lambda^{r3}$ (~20 to 100 molecules produced per cell cycle), extrinsic noise contributes significantly to the total noise even at the shortest time window (FIG. 4b). At longer time windows close to the length of a cell cycle, extrinsic noise dominates. As noise in protein production on the time scale of one cell cycle reflects noise in protein concentration in the absence of active degradation, this observation means that extrinsic noise also dominates the total noise in CI concentration at lysogenic expression levels. Hence, our observations caution against interpreting noise in protein concentration as the intrinsic stochasticity of gene expression, which is a reasonable approximation only at very low mRNA and protein expression levels[1,21,36] where the relative contribution of extrinsic noise is minimal.

Figure 4C:
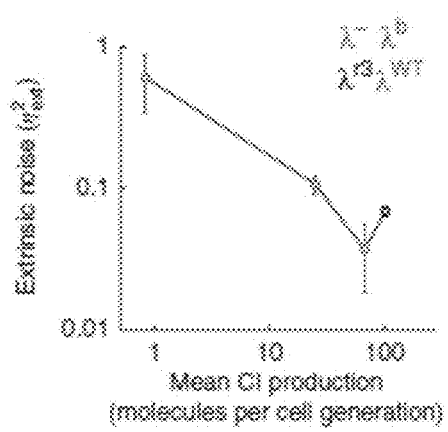
FIG. 4(c) shows extrinsic noise plotted against the mean CI production level in the four strains. Error bars are obtained by bootstrapping.
Figure 4D:
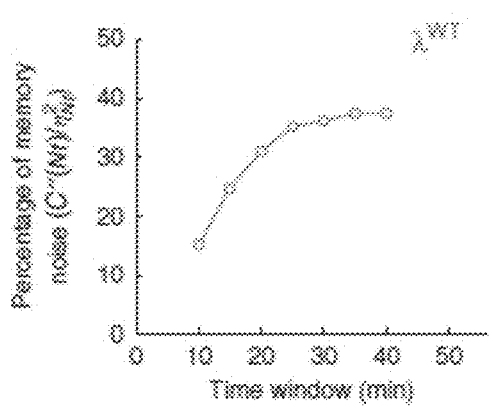
FIG. 4(d) shows the percentage of memory in total noise in $\lambda^{wt}$ at different time windows.

By comparing the relative contributions of extrinsic noise to total noise, we found that the total noise in $\lambda^{wt}$ had a lower relative contribution of extrinsic noise than in $\lambda^b$ and $\lambda^{r3}$ at time scales approaching one cell cycle (FIG. 4b). In $\lambda^{r3}$, extrinsic noise contributed ~80% of total noise at the 40-min time window, while in $\lambda^{wt}$, the contribution was reduced to ~30%. This observation is clearer in FIG. 4c where the extrinsic noise in each strain is plotted against the mean CI production level per cell generation. We observed a general dependence of extrinsic noise level on the mean CI production level in $\lambda^{wt}$, $\lambda^b$ and $\lambda^{r3}$, which was described previously in a genome-wide gene expression profiling study[1]. However, we found that the extrinsic noise in $\lambda^{wt}$ was significantly lower than that expected from the general expression level dependence, suggesting that negative autoregulation in $\lambda^{wt}$ may counteract extrinsic noise. Interestingly, while the extrinsic noise was lowered, $\lambda^{wt}$ exhibited significant, fast-decaying memory—memory contributed ~38% of total noise at 40-min time window (FIG. 4d) and decayed with a half life of ~20 min (FIG. 3a).

Taken together, these observations suggest important roles of the autoregulation of CI in determining the fate of a λ lysogen. We now understand that at the lysogenic CI concentration range, cell-to-cell heterogeneity in CI expression levels largely results of extrinsic noise rather than intrinsic stochasticity in CI production. Hence, lysogen stability can only be significantly increased by reducing the impact of extrinsic noise on CI expression. We show that a λ lysogen likely uses negative autoregulation to counteract extrinsic noise, ensuring that perturbations in CI expression do not have a long-lasting effect, which could be critical for lysogenic stability. An additional role of negative autoregulation is to decrease the CI expression level so that a λ lysogen may quickly lower CI concentration to induce lytic gene expression. The reduction of CI expression level increases intrinsic noise, but it likely does not significantly destabilize a lysogen given that intrinsic noise is not the major source of CI concentration fluctuations.

Implications of Intrinsic Stochasticity of CI Expression

The isolation of intrinsic noise from total noise enabled the extraction of the intrinsic Fano factor, an important indicator of intrinsic stochasticity of gene expression. The intrinsic Fano factors of all four strains were greater than one, consistent with non-Poissonian CI production. In addition, the nearly memoryless autocorrelation in $\lambda^-$, $\lambda^b$ and $\lambda^{r3}$ entailed the random occurrence of individual CI expression events in a time series[37,38]. These two observations suggest that CI molecules were produced in random bursts. Random, burst-like production of mRNA or protein molecules has been observed previously in experiments where the expression levels were low and individual expression bursts were clearly separated and followed in real time[5,15]. For relatively high expression levels where individual bursts could not be observed, bursty production was inferred from non-Poissoninan distributions of mRNA/protein molecules in cell populations[1, 14, 20, 21, 36]. While random, bursty production is the simplest explanation for stochastic gene expression, real biological systems may have more complex controls—feedback loops and multiple steps in transcription, translation and degradation could produce the same mRNA or protein distribution with different waiting time distributions between individual expression events[8,16,24]. Hence, the random bursting model cannot be automatically assumed. Here we used unique, time-dependent information about protein production noise to specifically determine that expression events occur randomly, providing higher confidence in the random bursting model.

We could not directly observe well-separated bursts in time traces for $\lambda^b$ and $\lambda^{r3}$ because of limited time resolution. However, in $\lambda^-$, where CI expression was repressed ~100 fold compared to $\lambda^3$, we observed small, well-separated production bursts (FIG. 2c, FIG. 15), demonstrating that protein bursting is possible from promoter $P_{RM}$. Under similar, highly repressed conditions, translational bursting, the production of multiple protein molecules from single mRNA molecules, was reported[5,39]. Our observation of protein bursting of a TF at moderate expression levels suggests that burst-like protein production may be a general mode of gene expression and a main source of intrinsic stochasticity.

In the random bursting model, the intrinsic Fano factor is linearly related to the final average protein burst size (Supplementary Information). The larger intrinsic Fano factors of $\lambda^b$, $\lambda^{wt}$ and $\lambda^{r3}$ compared to that of $\lambda^-$ suggest larger CI burst sizes in these strains. Because the random bursting model does not distinguish translational bursting from transcriptional bursting, the production of multiple mRNA molecules in one expression event, the observed CI burst size could be the result of combined translational and transcriptional bursting. Since mRNA molecules produced in all the strains are essentially identical in sequence, the increased burst size in $\lambda^b$, $\lambda^{wt}$ and $\lambda^{r3}$ most likely resulted from an increased number of mRNA molecules produced per burst rather than an increased number of protein molecules produced per mRNA.

Transcriptional bursting has been observed recently in both prokaryotic and eukaryotic cells[15, 20, 21, 23, 24, 36], but the biological causes are unclear. Interestingly, the presence of transcriptional bursting in $\lambda^b$, where the expression of CI is constitutive, suggests that transcriptional bursting may be an intrinsic property of the transcription process itself, independent of a TF. This suggestion corroborates with a recent study examining the noise in mRNA concentration for a set of E. coli promoters with different strengths and TF regulation details, which showed that regulation details had little influence on the burstiness of transcription[21].

Based on the random bursting model, the total CI expression level is the product of the bursting frequency and burst size. Therefore, the higher expression level of CI but similar intrinsic Fano factors in $\lambda^{r3}$ compared to those in $\lambda^b$ suggests that CI activates its own expression in $\lambda^{r3}$ primarily by increasing bursting frequency rather than burst size. The result is consistent with previous in vitro observation that CI increases the transcription initiation rate from $P_{RM}$[40].

Modulating bursting frequency rather than size could be important in maintaining low intrinsic fluctuations in CI expression—the random bursting model predicts that at the same expression level larger protein burst size leads to larger intrinsic noise. Zong et al., showed that decreased expression levels of a temperature sensitive CI mutant in a $\lambda$ lysogen at increasing temperatures resulted from reduced burst frequency, but not size, and that the stability of the lysogen is directly related to the burst frequency[36]. However, other TFs influence the frequency and size of transcriptional bursting in a variety of ways—in mammalian cells it has been observed that TFs could influence burst size only[20] or both burst size and frequency[24]. Further investigation on these differences may provide insight into molecular mechanisms underlying transcriptional bursting.

In this work we show that the CoTrAC strategy, combined with a time-dependent noise analysis, enabled the investigation of the influence of autoregulation on the stochastic expression dynamics of a TF in live E. coli cells at the single-molecule level. Our results show that different types of transcription regulation have little impact on the intrinsic stochasticity of CI expression, but mainly act on the extrinsic noise and memory of the system. These findings shed light on how a $\lambda$ lysogen uses autoregulation to minimize the noise in the expression of the fate-determining gene to maintain its extraordinary stability.

Methods

Bacterial Strains and Plasmids

The bacterial host strain for $\lambda^{r3}$, $\lambda^{wt}$, $\lambda^-$ and $\lambda^b$ is E. coli K12 MG1655 (Yale Genetic Stock). The genotype of each strain is listed in supplementary Table 51. To generate the $\lambda^{wt}$ strain, Phage $\lambda$ DNA (ind1sam7, Invitrogen) with the two point mutations corrected was used as a PCR template to generate a fragment of the $\lambda$ immunity region (cro through $O_L$). The rexA and rexB genes in the immunity region were removed and the tsr-venus-ub coding sequence was inserted in front of the cI gene. This fragment was then incorporated onto the chromosome of MG1655 at the lac operon site using $\lambda$ RED recombination[41]. The $\lambda^{r3}$, $\lambda^-$, and $\lambda^b$ strains were generated using site-directed mutagenesis. The pCG001 plasmid[42] harboring the deubiquitinating enzyme Ubp1 (gift from Rohan Baker at the John Curtin School of Medical Research, Australia) was transformed into chemically competent $\lambda^{wt}$, $\lambda^{r3}$, and $\lambda^-$ cells. Detailed procedures are described in Supplementary Information.

Culture Conditions

All cells were cultured in M9A media (M9/glucose minimal media supplemented with MEM amino acids; GIBCO) at 37° C. overnight with shaking Cells were reinoculated the next morning and harvested at mid-log phase ($OD_{600}\approx0.4$).

Time-Lapse Microscopy

Cells in mid-log phase were washed twice with M9A and resuspended at the dilution necessary to result in isolated single cells in microscope samples. Microscope samples were prepared on agarose gel pads as described previously[5], placed on an inverted microscope (IX-81, Olympus) equipped with a 100×, oil-immersion objective (Olympus), a 525-nm longpass filter (Chroma), and an emission filter (ET540×30 m, Chroma), and held at 37° C. using coverslide and objective heaters (Bioptechs). Cells were illuminated for imaging in brightfield mode or with widefield fluorescence. Fluorescent illumination was provided by the 514-nm line on an Innova Ion 1-308 laser (Coherent) with an illumination power density of 1 kW/cm². Excitation light was filtered with a 514-nm laser line filter (Semrock). Images were captured using a cooled EM-CCD (Andor Ixon DU888). An imaging algorithm built into the imaging software Metamorph (Molecular Devices) was used to automatically image up to 12 cells every five minutes (Supplementary Information below).

1.1 Construction of Four λ Strains

Synthetic oligonuecleotides (Invitrogen and IDT) used as primers in PCR reactions are listed in Table S2. Each pair is annotated as PX:PY below. Most PCR reactions utilized Platinum Taq polymerase (Invitrogen); site-directed mutagenesis used Pfu, PfuTurbo, or PfuUltra II (all from Stratagene); colony PCR for sequencing chromosome inserts used Taq (NEB) or DreamTaq (Fermentas). Restriction enzymes were from NEB. All plasmids and chromosome insertions were verified by sequencing (Genewiz).

To generate the four λ strains, phage λ DNA (ind1sam7, Invitrogen) was used as a PCR template (P1:P2) to generate a fragment of the λ immunity region (cro through $O_L$) flanked by BamHI sites. This DNA fragment was inserted into a BamHI-digested pUC19 vector (NEB) to generate plasmid pZH004. Transformations were carried out using chemically competent DH5α E. coli cells. The rexA and rexB genes in the immunity region were removed from plasmid pZH004 using inverse PCR (P3:P4 and subsequent blunt end ligation). The resulting plasmid was named pZH005. The immunity region (absent the rex genes) was then transplanted into pBR322 (NEB) using BamHI sites to make pZH012. The plasmid was then opened at the beginning of cI using inverse PCR (P7:P8) and blunt end-ligated in-frame with the ubiquitin-coding gene ub amplified (P5:P6) from a pBBR1MCS vector (gift from Daniel Finley). The resulting plasmid was named pZH014. A colony from strain SX4[1] served as a PCR template to generate an insert including a ribosome binding site and the tsr-venus membrane-targeted YFP gene; this fragment was ligated in-frame and N-terminal to ub-cI in pZH014 by adding XhoI and XmaI sites to the insert (P7:P8) and vector (P9:P10) by PCR to make plasmid pZH015. An Frt-KanR-Frt resistance cassette was then amplified from an SX4 colony with appended BamHI sites and inserted into pZH015 that had been partially digested with BamHI and gel purified to make pZH016.

Next, the ind1 and sam7 mutations in the λ immunity region were reverted to wild-type in two rounds of site-directed mutagenesis following the QuickChange protocol (Stratagene) to make pZH051. This $\lambda^{wt}$ immunity region, with rexA and rexB genes removed, and tsr-venus-ub inserted in front of cI, was then PCR amplified together with the KanR cassette (P11:P12) to transform into strain MG1655 harboring plasmid pKD46[2]. λ Red recombination was carried out to recombine the PCR fragment with the lac operon on the chromosome of strain MG1655[2]. Transformation followed a previously described protocol[2] and positive colonies were selected by growth on LB-kanamycin plates and blue/white screening and confirmed by sequencing the entire inserted region amplified by colony PCR (P13:P14). The temperature-dependent pKD46 plasmid was removed by growing at 37° C. The resulting strain was named $\lambda^{wt}$.

The resulting $P_{RM}$-tsr-venus-ub-cI transcript and the lysogenic $P_{RM}$-cI-rexA-rexB transcript differ in: 1. tsr-venus-ub-cI has a different gene coding sequence in the transcript. 2. the tsr-venus-ub-cI is translated from the lacZ ribosome binding site, while cI in the native transcript has a leaderless translation initiation site.

The plasmids pZH053, pZH052 and pZH055 carrying the $\lambda^{r3}$, $\lambda^-$, and $\lambda^b$ constructs, respectively, were generated by modifying pZH051 using site-directed mutagenesis. $\lambda^{r3}$ harbors the previously described r3 mutation[3] and is generated by PCR (P15:P16). In $\lambda^-$, the first codon of a in pZH051, ATG, is mutated to CTG (resulting in a methionine to leucine mutation) by PCR (P17:P18). The leucine residue in the resulting product is exposed when the protease Ubp1 cleaves between ubiquitin and CI, and the resulting CI protein is rapidly proteolyzed (with a mean lifetime of less than 3 min.) following the bacterial N-end rule[4,5]. As a result, there is virtually no CI present in the cell and thus Cro protein is expressed to strongly repress promoter $P_{RM}$. For $\lambda^b$, pZH052 is additionally mutated to eliminate cro expression by introducing a frameshift mutation by site-directed mutagenesis (P19:P20) so that the expression from $P_R$ results in a short peptide (MNNA) instead of the full-length Cro product. As a result, the repression of a by Cro is eliminated so that the basal activity of promoter $P_{RM}$ can be monitored. The three plasmids were recombined onto the chromosome of strain MG1655 as described for strain $\lambda^{wt}$, resulting in strains $\lambda^{r3}$, $\lambda^-$ and $\lambda^b$.

The plasmid pZH051-tsr used in the quantification of the molar ratio between the reporter and CI was generated by blunt end ligation of an inverse PCR product (P21:P22) to remove tsr from the tsr-venus-cI gene fusion in plasmid pZH051.

The final resulting Our $P_{RM}$-tsr-venus-ub-cI transcript and the lysogenic $P_{RM}$-cI-rexA-rexB transcript differ with respect to sequence, and our reporter-CI fusion is translated from the LacZ RBS rather than the non-canonical CI RBS; translation and transcript decay rates may differ between $\lambda^{wt}$ cells and lysogens."

1.2 Immunoblotting

Lysates were prepared from cell cultures in log phase, with the concentration normalized according to cell number determined by both cell counting in a Petroff-Hausser chamber and a plating assay. Protein electrophoresis was carried out using a 10% polyacrylamide gel in Tris-HCl (Bio-Rad) and the resulting gel was transferred to a PVDF membrane (Bio-Rad). CI bands were detected with anti-CI rabbit polyclonal antibody (Gift from John Little, University of Arizona) and goat anti-rabbit-HRP secondary antibody (Bio-Rad). Venus bands were detected using anti-GFP antibody (JL-8, Clontech) and goat anti-mouse-HRP secondary antibody (Bio-Rad). Purified recombinant GFP (Roche) was used to quantify the expression of proteins including the Venus sequence in anti-YFP blots. Immun-Star™ WesternC™ (Bio-Rad) reagents were used for luminescent visualization. Images were captured using HyBlotCL film (Denville), scanned, and quantified using the program ImageJ.

1.3 Calculation of Cleavage Efficiency

To quantify the molar ratio between the cleaved reporter and CI, we used a strain harboring a multi-copy plasmid, pZH051-tsr, which expresses a fusion protein Venus-Ub-CI under the promoter $P_{RM}$ without the membrane targeting sequence Tsr. We removed Tsr because we found that the much higher molecular weight of the Tsr-Venus-Ub protein resulted in a difference in the transfer efficiency during blotting compared to CI, which is approximately five-fold smaller in size. We loaded cells harboring this plasmid in the presence or absence of the protease Ubp1 in triplicate onto two protein gels and blotted one using an anti-Venus antibody and the other using an anti-CI antibody (FIGS. 5a-b). The same experiment was repeated independently three times. We calculated the molar ratio of Venus-Ub:CI after cleavage using the equation:

$$M_{\frac{Venus-Ub}{CI}} = \frac{I_{Venus-Ub}^{anti-Venus}}{I_{CI}^{anti-CI}} \cdot \frac{I_{Venus-Ub-CI}^{anti-CI}}{I_{Venus-Ub-CI}^{anti-Venus}} \quad (S1)$$

Here, I is the intensity of the protein band specified by the subscript. The superscript indicates whether the protein band was detected using an anti-Venus or anti-CI antibody. The averaged Venus:CI ratio is 1.1±0.1. Based on the number of cells loaded in each lane (1.2 million) and the relative intensity of 1 ng of GFP, the cleaved samples in FIG. 5a (lanes 4 to 6) contain approximately 7,000 Venus-Ub molecules per cell. No uncleaved band is seen at this high expression level, demonstrating the highly efficient cleavage by Ubp1.

1.4 Quantifying CI Expression Via Multiple Methods

FIG. 6a shows the results of 3 parallel, independent methods of calculating CI expression. The results of our timelapse experiments (the number of CI molecules produced per generation) were compared to the integrated steady-state fluorescence intensity of single cells as well as the number of CI molecules expressed per cell calculated from immunoblots detecting either CI or YFP. To compare results from different methods, all expression levels were normalized to CI expression in $\lambda^{wt}$. When available, error bars represent the standard deviation of independent measurements using a particular method (measures of error are not always available; i.e. for $\lambda^{wt}$ Western blots, expression levels are normalized to $\lambda^{wt}$ measurements so error estimates are only available for other strains). We find that our single-cell, timelapse measurements are indistinguishable from alternative measurement methods within error. We also see that CI expression in a wild-type $\lambda$ lysogen is comparable to that in $\lambda^{wt}$ (~75% of $\lambda^{wt}$ expression), indicating that CI should be near its wild-type concentration in experiments utilizing $\lambda^{wt}$, and thus subject to regulatory mechanisms relevant to $\lambda$ lysogeny.

1.5 Time-Lapse Imaging Acquisition Sequence

We used a custom built imaging sequence to acquire images every five minutes:
  i. Move to a stored cell location
  ii. Autofocus using Metamorph software
  iii. Center cell in viewfield
  iv. Take brightfield image for cell segmentation
  v. Take 6 fluorescence images (100-ms each) at 1-second intervals It was found that, although a large majority of Venus molecules are fluorescent in the first frame, some molecules turn on randomly (blinking on a timescale of seconds has been reported for YFP[6]. Therefore, we incorporated a 1-second dark time between subsequent exposures to allow a new dark-bright equilibrium between Venus fluorophores to be reached. About half of the Venus molecules bleach in the first frame. For image analysis, the sixth image acquired was subtracted from the first to correct for uneven background intensity and minimize contributions from unbleached molecules. Because the imaging timescale (a few seconds) is much shorter than the timescale of cell growth, and because Tsr-Venus-Ub molecules usually translocate to the cell pole before chromophore maturation, unbleached molecules rarely move during image acquisition.

1.6 Steady State Microscopy

Samples were prepared and imaged as described above, but samples were less dilute so that multiple cells could be analyzed in single images. Cells were kept at room temperature and imaged immediately after sample preparation so that no substantial cell growth was observed during data acquisition.

1.7 Image Analysis and Time Trace Generation

Figure 7A:
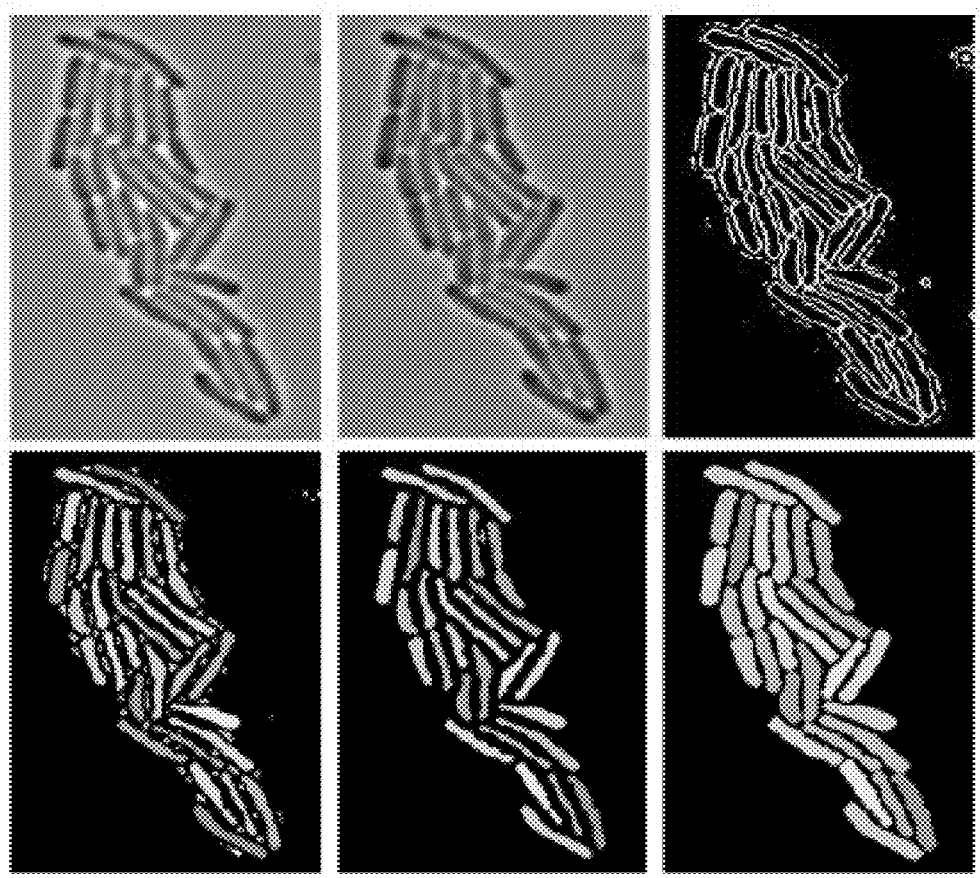
FIG. 7(a) shows brightfield images segmented using a custom MATLAB routine. Images are first filtered before being segmented (using a Laplace-of-Gaussian method). Objects above a size threshold are retained and assumed to be cells. Movies are then analyzed manually to repair poor segmentation. Lastly, cells in movies are assigned to cell lineages.
Figure 7B:
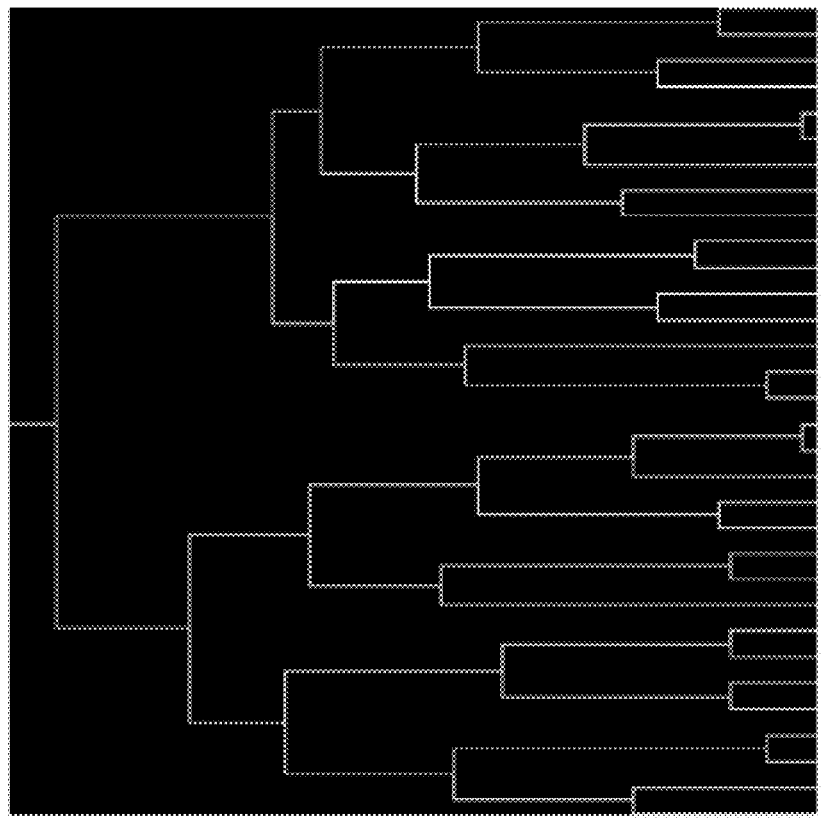
FIG. 7(b) shows an example set of lineages corresponding to the colony in 7(a).
Figure 7C:
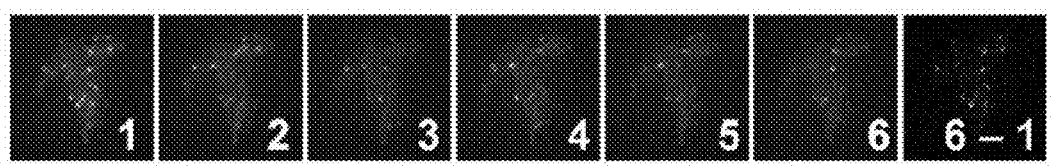
FIG. 7(c) shows fluorescence imaging routine; 6 images are acquired at 1-second intervals. Most molecules bleach over this period; a small number of molecules become fluorescent during imaging because the Venus chromophore matures or the molecule blinks from the off to the on state. For analysis, the sixth image is subtracted for the first to approximately account for unbleached molecules and eliminate autofluorescent background.

For every frame in timelapse movies, images of E. coli colonies were segmented using a custom MATLAB routine (FIGS. 7a-c). Individual frames were aligned with each other by aligning the center of mass of each segmented image. Generally, cell lineages could then be assigned using an automated MATLAB script based upon which cells overlapped in subsequent frames; lineage assignments were checked manually and corrected when necessary.

The fluorescence images described above were processed in MATLAB to identify spots generated by one or more Venus molecules. Images were processed as follows:
  i. Bandpass filter to reduce high-frequency noise and low-frequency variability (cell background, etc)
  ii. Threshold
  iii. Delete objects in thresholded image below a size cutoff Once fluorescent spots were detected, the raw fluorescence image was then used to estimate spot intensity. Spots were then fit by a two-dimensional Gaussian function:

$$I = A + Be^{-\frac{(x-x_0)^2 + (y-y_0)^2}{2\sigma^2}} \quad (S2)$$

Initially, the $\sigma$ parameter is fixed to acquire a good guess for $x_0$ and $y_0$. The fit is then refined with more parameters using the function:

$$I = A + Be^{\frac{u^2}{2\sigma_u^2} + \frac{v^2}{2\sigma_v^2}}, \text{ where} \quad (S3)$$

Figure 8:
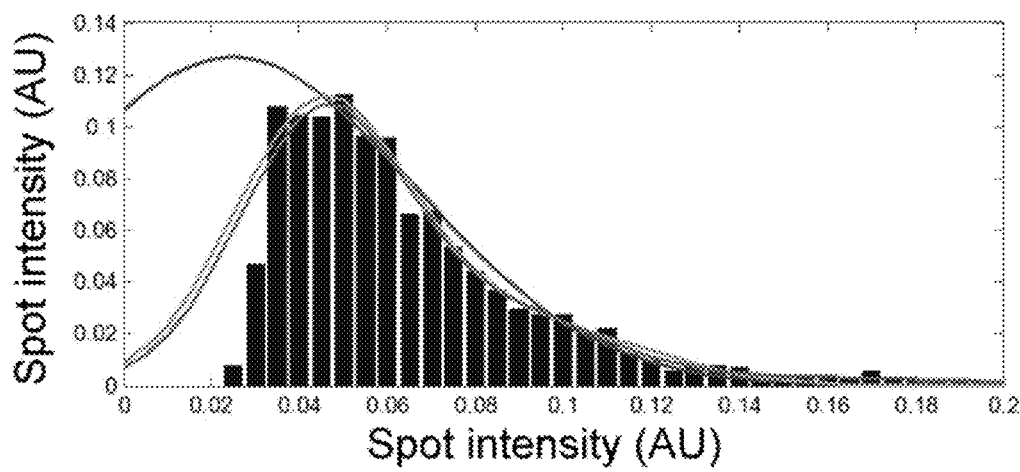
FIG. 8 shows an integrated fluorescence intensity distribution of spots (N=1526) detected in time traces of $\lambda^{-}$. The histogram is well fit by the sum of two (purple) or three (green) normal distributions with quantized means of ~0.05. A single normal distribution (red) does not fit the data well. The mean intensity value also agrees with in vitro single-molecule measurement of purified Venus molecules. Note low-intensity data (intensity less than 0.035) was not used in the fit due to the following considerations: (a) a number of single-molecule expression events (~10% assuming the distribution shown here) are too weak to be detected in YFP images. This is expected since photobleaching is generally an exponential process and some molecules will photobleach quickly; (b) some molecules will photobleach while an image is being acquired, yet still emit sufficient photons to be detected; (c) a normal distribution of spot intensities is an empirical approximation based on the assumptions that emission from a single molecule continues for most of a frame, that the number of photons emitted during a given time follows a Poisson distribution, and that quantum yield and the probability of detecting an emitted photon are independent of molecule orientation and the position of focal plane, etc. In practice, the effects listed above will generally result in somewhat higher probabilities at low intensity than that can be experimentally measured.

$u = (x - x_0)\cos\theta + (y - y_0)\sin\theta$, and $v = (x - x_0)\sin\theta + (y - y_0)\cos\theta$ This function accounts for oblong spots, including those that are not oriented along the x- or y-axis; this is important since, while spots in our experiments are found at cell poles, they do not necessarily correspond to immediately adjacent molecules (i.e. the image of two molecules separated by 50 nm will be oblong rather than radially symmetric). We find that this largely empirical fitting procedure produces well quantized integrated intensities (FIG. 8). The integrated intensity is proportional to $B\sigma_u\sigma_v$. The intensity of a single molecule was determined from movies of $\lambda$ growth, in which only zero, one, or a few molecules are visible at any time. Detected spots were assigned to the closest cells in the segmented image.

Fluorescent molecules that are too dim due to reasons such as early photobleaching may not be counted. We show below (Section 3.3.2) that the false negative effect does not change the nature of distribution. Instead, it changes the average protein burst size—the real burst size when all single protein molecules are counted would be larger than our experimentally measured burst size. Since the chance of missing some molecules due to early bleaching is the same for all four $\lambda$ strains, the ratio of burst sizes between the strains is maintained.

1.8 Steady-State Fluorescence Analysis

Images of multiple cells in single frames were segmented as described above. The fluorescence background was estimated by the average intensity of the portion of images not occupied by cells; this produced reasonable results as the expression level within cells in the strains examined was high enough to generate a YFP signal much greater than the cells' autofluorescent background (except for $\lambda^-$). The number of Venus molecules in a cell was thus approximately proportional to the total integrated fluorescence intensity of a cell, corrected for the fluorescence background.

2. Supplemental Data Analysis

Figure 9:
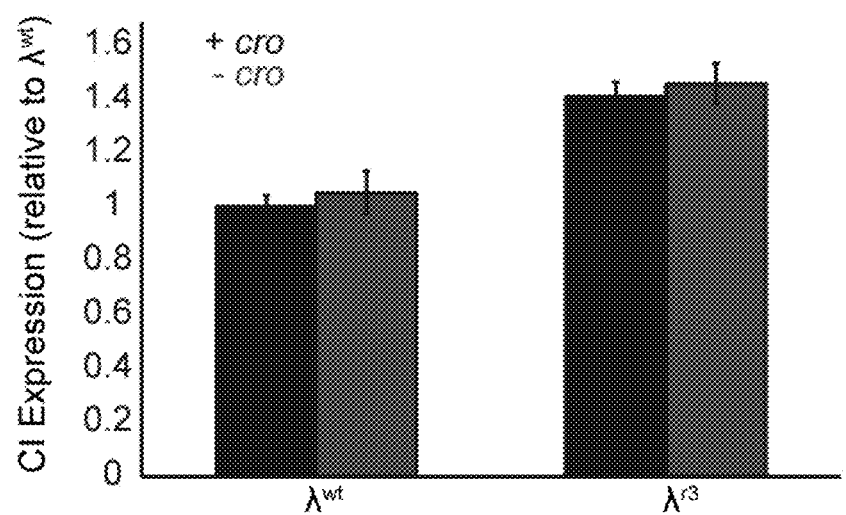
FIG. 9 shows CI expression levels in the $\lambda^{wt}$ and $\lambda^{r3}$ (no negative feedback) strains with and without cro are indistinguishable within error, showing that cro expression in $\lambda^{wt}$ and $\lambda^{r3}$ is unlikely to contribute to differences observed in $\lambda^b$, where the cro gene is deleted. Values are determined from steady-state fluorescence experiments and normalized to the intensity of $\lambda^{wt}$ cells with cro. Error bars show the standard error.

2.1 CI expression is not significantly affected by Cro in $\lambda^{r3}$ and $\lambda^{wt}$ We measured the steady-state level of CI expression by integrating single-cell fluorescence for strains $\lambda^{r3}$ and $\lambda^{wt}$ as well as in equivalent strains with cro removed by site-directed mutagenesis as in $\lambda^b$. FIG. 9 shows that expression in the two strains in the absence of cro is not significantly different from that in the presence of cro. Thus, differences in $P_{RM}$ activity between $\lambda^b$ and $\lambda^{r3}$ are due to the inactivation of CI and not from any effect of Cro binding.

2.2 Cell-Cycle Length Distribution

Figure 10:
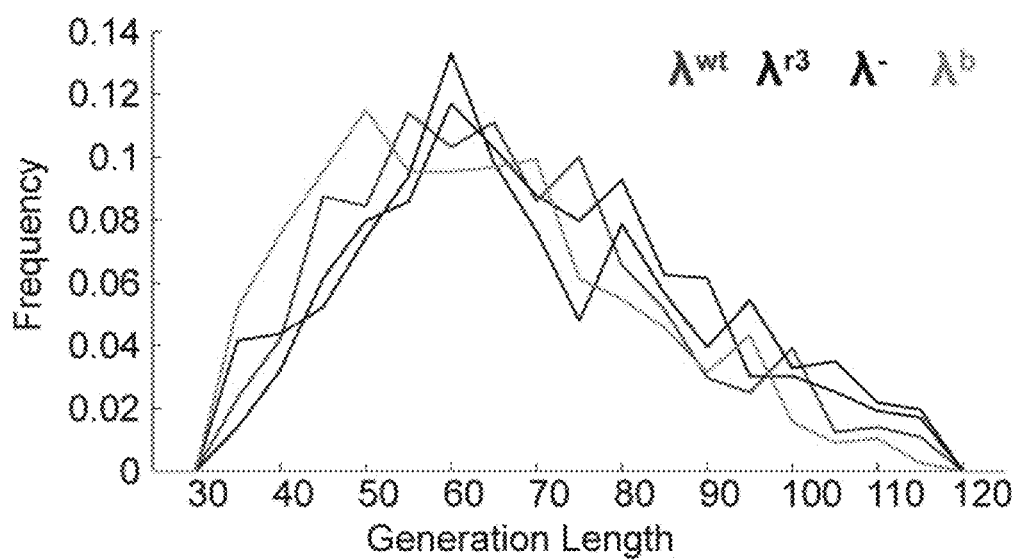
FIG. 10 shows histograms of cell generation lengths in minutes show that cell growth is similar in all strains and that the difference in CI expression levels in the four strains is not the result of different cell generation lengths.

We generated histograms of the observed cell cycle lengths in time traces of all four strains and found them to be indistinguishable from each other within experimental uncertainties (FIG. 10). We did not use cells that have extremely short or long cell cycle lengths, which may be indicative of abnormal physiological states. For analyses discussed in the main text, we selected cells that have a cell cycle length between 45 and 100 min.

2.3 Linear Correction for Cell-Cycle Dependence

Figure 11:
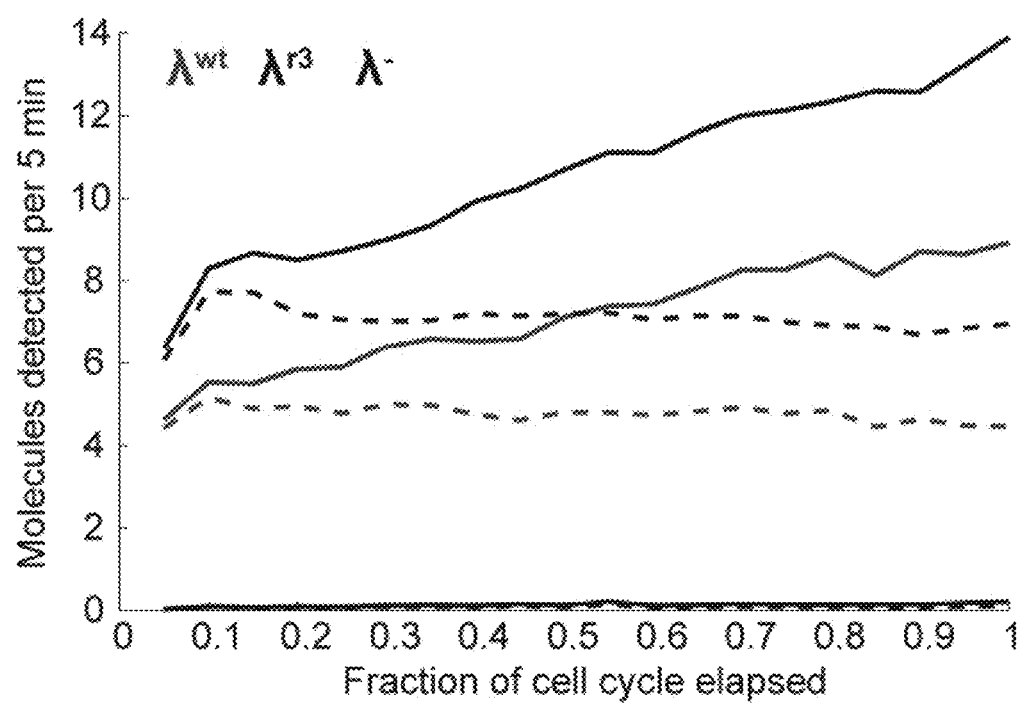
FIG. 11 shows the number of molecules detected for raw (solid) and cell-cycle-corrected (dashed) time traces by the fraction of a cell cycle elapsed (e.g. an observation at 15 min. in a 60-min. cell cycle maps to 0.25) and averaged.

During the bacterial cell cycle, the number of chromosome copies, and thus the copy-number of a particular gene, doubles. We observed that, averaged over all time traces, the CI expression rate increased linearly throughout a cell cycle and doubled at the end of the cell cycle (FIG. 11). This linear increase is counterintuitive if one assumes that the expression rate should only double at the moment a gene is replicated. Nevertheless, a number of studies have observed similar effect[7,8]. This effect could be due to reasons that our estimation of when a cell cycle begins and ends is inexact, obfuscating any discrete increase in expression, and/or that the time of gene doubling varies substantially between cells. We corrected the cell-cycle dependence of CI expression by assuming that the rate of CI production at the end of cell cycle exactly doubles that at the beginning of the cell cycle to create a corrected time series of CI expression per 5 min., n(t), from the observed time trace, n'(t), given a cell-cycle length of T:

$$n(t) = \frac{n'(t)}{1 + \frac{t}{T}} \tag{S4}$$

All the data reported in this work are corrected using Eq. (S4).

2.4 the Effect of the Linear Correction on Noise and Fano Factor

The linear correction (Eq.S4) for cell-cycle dependence does not change the noise $\sigma^2/\mu^2$, because both the mean, $\mu$, and standard deviation, $\sigma$, are scaled in the same way. However, the linear correction will reduce the Fano factor, $\sigma^2/\mu$. For example, for a set of random numbers n with a Fano factor F, if each number n is divided by a factor a, the resulting Fano factor will be F/a:

$$\frac{\langle (\frac{n}{a})^2 \rangle - \langle \frac{n}{a} \rangle^2}{\langle \frac{n}{a} \rangle} = \frac{1}{a}\frac{\langle n^2 \rangle - \langle n \rangle^2}{\langle n \rangle} = \frac{F}{a} \tag{S5}$$

For a CI production time trace, if the cell-cycle-dependent increase in CI production rate is caused by increased expression frequency but not the size of each expression event, the true Fano factor, which we show to be determined by burst size but not frequency in Section 3.2, should remain a fixed value. However, the mathematical treatment to correct the cell-cycle dependence will cause the Fano factor directly calculated from the corrected data to be artificially smaller than the true one in the absence of cell-cycle dependence. Further, since the number of CI molecules measured at a particular time, n'(t), is corrected using a different coefficient a(t) (between 1 and 2) according to its position in the cell cycle, the true Fano factor can not be simply calculated by scaling the Fano factor with a fixed value as shown in Eq. S5.

In the following we show that the true Fano factor of CI production in the absence of correction for cell-cycle dependence, F', should take the form of F'=F/ln(2), where F is the Fano factor directly calculated from data after linear correction.

We assume a protein production time series that has a fixed Fano factor, F', but an average protein production rate that doubles linearly through a cell cycle of length T. In the whole series, we approximate that during the time interval from mt to (m+1)t the expression frequency is constant. Therefore, the average number of protein molecules $\langle n'(t) \rangle$ produced during such a time window can be expressed as:

$$\langle n'(t) \rangle = a(t) \langle n \rangle \tag{S6}$$

Here, the coefficient is a constant with the value a(t)=1+t/T, and $\langle n \rangle$ is the mean protein production rate in the absence of cell-cycle dependence. Correspondingly, the Fano factor calculated using data from the same time window equals F' with $F' = (\langle n'^2(t) \rangle - \langle n'(t) \rangle^2)/\langle n'(t) \rangle$. After linear correction we have a new time series:

$$n(t)=n'(t)/a(t), \langle n(t) \rangle = \langle n'(t) \rangle / a(t) = \langle n \rangle \tag{S7}$$

In principle, the true Fano factor F' can be calculated by dividing CI production time traces into multiple time windows such as $1^{st}$, $2^{nd}$, and $3^{rd}$ 5-min. windows, and only using data in the same time window from different cells. However, this treatment will reduce the available sample size, leading to an increased uncertainty in the calculated Fano factor. In addition, variations in cell-cycle length (FIG. 10) would complicate this calculation. Therefore, we take the following approach by showing that the total variance of the time series after linear correction is the variance at each time window integrated over all available time windows:

$$\sigma^2 = \frac{1}{T}\int_0^T dt \left[ \left\langle \left(\frac{n'(t)}{a(t)}\right)^2 \right\rangle - \left\langle \frac{n'(t)}{a(t)} \right\rangle^2 \right] \tag{S8}$$
$$= \frac{1}{T}\int_0^T dt \frac{F'}{a}\left\langle \frac{n'}{a} \right\rangle$$
$$= \frac{F'\langle n \rangle}{T}\int_0^T dt \frac{1}{a(t)}$$
$$= F'\langle n \rangle \ln(2) \Rightarrow F$$
$$= \frac{\sigma^2}{\langle n \rangle}$$
$$= \ln(2)F'$$

Eq. S8 shows that the true intrinsic Fano factor, F', can be calculated from the Fano factor after correction, F, as: F'=F/ln(2). All the Fano factors we reported in Table 1 are adjusted using the 1/ln(2) factor. The intrinsic Fano factors listed in Table 1 are the fitted intrinsic Fano factor obtained from the noise curve, then adjusted using the 1/ln(2) factor.

2.5 Presence of a Slow Variation in CI Production Rate

We examined the time scale at which temporal fluctuations of a CI production time trace approach the population level. If there are no extrinsic differences between different cell lineages, the temporal noise of a CI production time trace would equal to that of the population at any given time.

We calculated the noise in the CI production rate (number of CI molecules expressed per 5 min.) using time windows of different lengths within individual long cell lineage traces. We then averaged the noises calculated using time windows of the same length from different cell lineages. The resulting mean noise is then plotted against the length of the time window used and compared with the population noise level. FIG. 12 shows that the noise at long time windows is larger than that at short time windows, indicating that variation within lineages is smaller than that between lineages. Furthermore, the noise gradually approaches population noise level in ~4 cell cycles, indicating that this noise operates on a time scale longer than a single cell generation. This observation is indicative of the presence of cell-to-cell heterogeneity, or extrinsic noise as termed in previous studies. The long time scale of extrinsic noise allowed us to approximate it as a constant on the time scale of one cell cycle.

2.6 Calculation of Autocorrelation

We used time traces of single cell generations that are between 45 and 100 minutes long. To ensure that each cell has equal contribution to different time lags, we truncated all time traces at 45 min. We calculated the autocorrelation at different time lags, $\tau$, for each time trace according to the following equation:

$$C(\tau) = \sum_{i,j} \left( \frac{1}{N} n_j(i) * n_j(i+\tau) \right) - \left[ \frac{1}{N} \sum_{i,j} n_j(i) \right] * \left[ \frac{1}{N} \sum_{i,j} n_j(i+\tau) \right] \quad (S9)$$

Where index j is the jth cell and index i is the ith frame of data point in the time trace of cell j.

$$N = \sum_{i,j} 1$$

is the total number of data pairs for a given time lag.

For $\lambda^{wt}$, we observed an autocorrelation decay time ~20 min. For the other three strains, we observed a rapid decay at the first 5-min time lag, and a relatively constant plateau at longer time lags. To verify whether these observation are still valid in long time traces, we computed autocorrelation of all the four strains using long cell lineages that span more than one generation. The resulting autocorrelation is similar to what was observed using single generation time traces. The time it takes for the autocorrelation to drop to half of the initial value at first time lag is ~20 min for in $\lambda^{WT}$, ~50 min for $\lambda_{R3}$, and difficult to estimate for $\lambda^b$ and $\lambda^-$ because of their low correlation values with large error ranges (FIG. 13). The decay time for $\lambda^{r3}$ is significantly slower than that of $\lambda^{wt}$: it approaches the length of one cell cycle, consistent with the relative constant autocorrelation values calculated using single generation time traces (longest time window at 40 min). While we can also subtract this low correlation out from the total noise of $\lambda^{r3}$ as what we did for $\lambda^{wt}$ (Section 3.1.3), it does not improve the noise curve fitting goodness significantly for $\lambda^{r3}$.

2.7 Estimation of Intrinsic and Extrinsic Noise Using Different Methods

We estimated intrinsic and extrinsic noise of the four strains using four different methods: autocorrelation, noise curve, correlation pairs, and a previously described method estimating extrinsic noise from averaged production over cell cycles[9]

Autocorrelation:

We computed the autocorrelation for CI expression per 5 min. for each strain. For $\lambda^{r3}$, $\lambda^-$ and $\lambda^b$, we took the average of the autocorrelation values after the zero time lag as the variance of extrinsic noise and then divided it by the square of the mean CI production rate to estimate the magnitude of extrinsic noise. The autocorrelation of CI expression in $\lambda^{wt}$ does not fall to zero quickly, so the extrinsic variance was taken as the average of the last two time lags. The extrinsic noise estimated from autocorrelation curve is higher than that obtained with noise curve analysis, because the autocorrelation curve is too short to reach the true plateau. Therefore, extrinsic noise estimations using this method can be regarded as the upper bounds of extrinsic noise.

Noise Curve:

For each time trace of a single cell generation between 45 and 100 min., we summed the total number of CI molecules $n_{Nt}$ produced in N subsequent time windows using all possible time window positions. We then calculated the noise $\eta^2$ in $n_{Nt}$ obtained at the same time window from all time traces. Because the sample sizes at long time windows are smaller than those at short time windows, we truncated the noise curve at the 40-min. time window. The resulting noise curve is fitted with function y=A/x+B. The intrinsic noise at 5-min time window is calculated using the fitted intrinsic Fano factor A adjusted using the 1/ln 2 facto, and then divided by the mean expression level of CI at the 5-min window for each strain. The fitted value B is taken as the extrinsic noise according to Eq. 4 in the main text.

Correlation Pairs:

We show in FIG. 12 that extrinsic noise operates on a time scale of several cell cycles. Therefore, for two adjacent frames in a time series, the extrinsic noise can be approximated as constant. The difference in the number of CI molecules produced in the two adjacent frames can then be regarded as arising from intrinsic noise. The difference in the numbers of CI molecules produced in two non-adjacent time points then contains greater contribution from extrinsic noise. In an approach analogous to a previous method using two fluorescent reporters[10], every pair can be regarded as a cell in which there are two reporters. The intrinsic and extrinsic noise can be estimated using equations:

$$\eta_{int}^2 = \frac{\langle (n_1 - n_2)^2 \rangle}{2 \langle n_1 \rangle \langle n_2 \rangle} \text{ and } \eta_{ext}^2 = \frac{\langle n_1 n_2 \rangle - \langle n_1 \rangle \langle n_2 \rangle}{2 \langle n_1 \rangle \langle n_2 \rangle} \quad (S10)$$

Here, $n_1$ and $n_2$ are the numbers of CI molecules produced in two adjacent time frames. For a time trace of CI production, all possible adjacent pairs are used in the calculation. We note that this method is valid only when each time frame is independent of adjacent time frames, i.e. there is no correlation. This assumption is reasonable for $\lambda^{r3}$, $\lambda^-$ and $\lambda^b$ strains, but does not hold for $\lambda^{wt}$. As a result, the extrinsic noise of $\lambda^{wt}$ estimated using this method is significantly higher than the true extrinsic noise.

Cell-Cycle Average:

We also used a previously-described method[9] to estimate extrinsic noise. In this method, the extrinsic noise is considered constant on the time scale of one cell cycle. The difference in the mean CI production rates averaged over one cell cycle for different cells can then be regarded as extrinsic noise if intrinsic noise is averaged out during one cell cycle. Therefore, extrinsic noise can be calculated using the following equation:

$$\eta_{ext}^2 = \frac{\overline{\langle n \rangle^2} - (\overline{\langle n \rangle})^2}{(\overline{\langle n \rangle})^2} \tag{S11}$$

Here, <n> is the mean CI production rate average over one cell cycle for each cell, and the overbar indicates the average of <n> over all cells. The corresponding intrinsic noise is then what is left of the total noise after the subtraction of extrinsic noise. Note that extrinsic noise estimated using this method is always larger than that estimated using the other three methods because intrinsic noise cannot be completely averaged out in one cell cycle. This is the case especially for $\lambda^-$ and $\lambda^b$ strains because their low expression levels result in relatively high intrinsic noise.

2.8 Estimation of Error Bars

Error bars for all the measurements except the mean CI production rate of each strain were obtained by bootstrapping 1000 samples randomly selected with replacement from the original data set using the bootstrp function in Matlab. For example, the noise measurement of $\lambda^{r3}$ (0.32±0.01) was obtained by randomly selecting data points from the original data set, computing the noise ($\sigma^2/\mu^2$) for the new sample, and then repeating this process 1000 times. The error bar reported is the standard deviation of the noise calculated from 1000 samples.

3. Theoretical Modeling 3.1 Time-Dependent Noise Curve Analysis 3.1.1 Total Noise Total protein expression noise can arise from intrinsic and extrinsic sources. Extrinsic noise was introduced to indicate the expression noise due to the fluctuations of biochemical reaction rates. FIG. 12 shows that noise exists on a timescale greater than one cell cycle, which can be approximated as constant, uncorrelated fluctuations of a dynamic parameter θ from cell to cell (a general parameter that collectively describes extrinsic factors that influence gene expression)[9,11]. We call this "extrinsic noise" to be consistent with other work, but note that extrinsic effects (those common to many genes) can exist at all timescales. Fluctuations of biochemical reaction rates on faster timescales will make the waiting time between productions events non-exponentially distributed even within a cell cycle, which can considered as part of memory for the production processes. Such contribution of memory to the total protein production noise will be analyzed in SI 3.1.3. Here we first focus on the extrinsic noise due to static fluctuations of reaction rates from cell to cell.

Cells with the same parameter θ will have the same probability distribution of the number of protein molecules expressed in a given time window. Accordingly, the average number of CI molecules produced during for a cell cycle of length t with a given θ is:

$$\langle n \rangle(t) = g(\theta)t$$

For a cell cycle sufficiently long to average out intrinsic fluctuations:

$$\eta_{ext}^2 \approx \frac{\overline{\langle n \rangle^2(t)} - (\overline{\langle n \rangle(t)})^2}{(\overline{\langle n \rangle(t)})^2} = \tag{S12}$$

$$\frac{\overline{g^2(\theta)t^2} - (\overline{g(\theta)t})^2}{(\overline{g(\theta)t})^2} = \frac{\overline{g^2(\theta)} - (\overline{g(\theta)})^2}{(\overline{g(\theta)})^2} = const$$

Here the average over parameters θ is indicated with an overbar, i.e., $$\overline{g(\theta)t} = \int p(\theta)g(\theta)t d\theta = t\int p(\theta)g(\theta)d\theta = t\overline{g(\theta)}$$

$$\overline{g^2(\theta)t^2} = \int p(\theta)g^2(\theta)t^2 d\theta = t^2\int p(\theta)g^2(\theta)d\theta = t^2\overline{g^2(\theta)} \tag{S13}$$

where p(θ) is the probability of a certain parameter θ. In this way, the extrinsic noise is a constant independent on the observation time window, t. Then, the total noise can be written as:

$$\eta_{tot}^2 = \frac{\overline{\langle n^2 \rangle(t)} - (\overline{\langle n \rangle})^2}{(\overline{\langle n \rangle})^2} = \tag{S14}$$

$$\frac{\overline{\langle n \rangle^2(t) - (\langle n \rangle(t))^2}}{(\overline{\langle n \rangle(t)})^2} + \frac{\overline{\langle n \rangle^2(t)} - (\overline{\langle n \rangle(t)})^2}{(\overline{\langle n \rangle(t)})^2} = \eta_{int}^2 + \eta_{ext}^2$$

Thus, the extrinsic noise will contribute a constant term in the total time dependent noise, $\eta_{tot}^2$.

3.1.2 Correlation and Extrinsic Noise:

We first assume that CI production time traces n(θ,t) are dependent on the general parameter θ, and that θ is constant on the time scale of one cell cycle. If a time trace with such a fixed parameter θ is not correlated:

$$\langle n(\theta,t)n(\theta,t')\rangle = \langle n(\theta)\rangle^2$$

and that time traces with different θ are independent on each other:

$$\langle n(\theta,t)n(\theta',t')\rangle = \langle n(\theta)\rangle\langle n(\theta')\rangle$$

the auto correlation function of these time traces is:

$$C(t-t') = \int d\theta p(\theta)\langle n(\theta, t)n(\theta, t')\rangle - \left(\int d\theta p(\theta)\langle n(\theta, t)\rangle\right)^2 = \tag{S15}$$

$$\int d\theta p(\theta)\langle n(\theta)\rangle^2 - \left(\int d\theta p(\theta)\langle n(\theta, t)\rangle\right)^2 = \overline{\langle n(\theta)\rangle^2} - (\overline{\langle n(\theta)\rangle})^2 \neq 0$$

Here, p(θ) is the probability that a generation has a certain parameter θ. This equation shows that the autocorrelation for a process that is memoryless but has extrinsic noise is time independent and will have a non-zero constant value, which is the variance of extrinsic noise.

In general, if the process has memory but the parameter θ is still constant on the time scale of one cell cycle:

$$\langle n(\theta,t)n(\theta,t')\rangle - \langle n(\theta)\rangle^2 = C_\theta(t-t') \neq 0$$

The total autocorrelation can be decomposed into two parts:

$$C(t-t') = \int d\theta p(\theta)\langle n(\theta, t)n(\theta, t')\rangle - \left(\int d\theta p(\theta)\langle n(\theta, t)\rangle\right)^2 = \tag{S16}$$

$$\int d\theta p(\theta)\langle n(\theta, t)n(\theta, t')\rangle - \int d\theta p(\theta)\langle n(\theta)\rangle^2 +$$

-continued $$\int d\theta p(\theta)\langle n(\theta)\rangle^2 - \left(\int d\theta p(\theta)\langle n(\theta,t)\rangle\right)^2 =$$

$$\int d\theta p(\theta) C_\theta(t-t') + \overline{\langle n(\theta)\rangle^2} - (\overline{\langle n(\theta)\rangle})^2 =$$

$$\int d\theta p(\theta) C_\theta(t-t') + const = C'(t-t') + \sigma_{ext}^2$$

The constant term is the contribution of extrinsic fluctuations and the time-dependent term measures the memory of the production process.

It provides a way to estimate the extrinsic noise from the autocorrelation function: the non-zero plateau of the autocorrelation function is $\sigma_{ext}^2$ and the extrinsic noise is $$\eta_{ext}^2 = \frac{\sigma_{ext}^2}{\langle n\rangle^2}.$$

The pure temporal memory part of the autocorrelation is then: $C'(t-t') = C(t-t') - \sigma_{ext}^2$.

3.1.3 Relation Between Time-Dependent Noise and Autocorrelation

We assume a general stochastic process in which the number of protein molecules produced in the time window (0,t) is $n_1$, and $n_2$ in the time window (t,2t). Both $n_1$ and $n_2$ satisfy the same distribution of $P(n,t)$, $\langle n_1\rangle = \langle n_2\rangle = \langle n\rangle$, and $\langle n_1^2\rangle = \langle n_2^2\rangle = \langle n^2\rangle$. Therefore, the total number of molecules produced during time window (0,2t) is $n_1+n_2$, with:

$$\langle n_1 + n_2\rangle = 2\langle n\rangle_t \quad (S17)$$

$$\langle (n_1 + n_2)^2\rangle =$$
$$\langle n_1^2 + n_2^2 + 2n_1n_2\rangle = 2\langle n^2\rangle + 2\langle n_1n_2\rangle = 2\sigma_t^2 + 2C(t) + 4\langle n\rangle_t^2$$

$$\frac{\sigma_{2t}^2}{\langle n\rangle_{2t}^2} = \frac{\langle (n_1+n_2)^2\rangle - \langle n_1+n_2\rangle^2}{\langle n_1+n_2\rangle^2} = \frac{1}{2}\frac{\sigma_t^2}{\langle n\rangle_t^2} + \frac{1}{2}\frac{C(t)}{\langle n\rangle_t^2}$$

where C(t) is the correlation function between two successive time intervals (or time windows). When the correlation is 0, we have:

$$\frac{\sigma_{2t}^2}{\langle n\rangle_{2t}^2} = \frac{1}{2}\frac{\sigma_t^2}{\langle n\rangle_t^2} \quad (S18)$$

Similarly, if the number of molecules produced in time window (0,Nt) is $n_1+n_2+\ldots n_N$, we have:

$$\langle n\rangle_{Nt} = \langle n_1 + n_2 \ldots + n_N\rangle = N\langle n\rangle_t \quad (S19)$$
$$\langle (n_1 + n_2 \ldots + n_N)^2\rangle =$$
$$N\sigma_t^2 + 2[(N-1)C(t) + (N-2)C(2t) + \ldots + C(Nt-t)] + N^2\langle n\rangle_t^2$$

$$\eta_{Nt}^2(t) = \frac{\sigma_{Nt}^2}{\langle n\rangle_{Nt}^2} = \frac{\langle (n_1+n_2\ldots+n_N)^2\rangle - \langle n_1+n_2\ldots+n_N\rangle^2}{\langle n_1+n_2\ldots+n_N\rangle^2} =$$

$$\frac{1}{\langle n\rangle_{Nt}}\cdot\frac{\sigma_t^2}{\langle n\rangle_t} + \frac{2[(N-1)C(t)+(N-2)C(2t)+\ldots+C(Nt-t)]}{\langle n\rangle_{Nt}^2} =$$

$$\frac{1}{\langle n\rangle_{Nt}}\frac{\sigma_t^2 - \sigma_{ext}^2}{\langle n\rangle_t} + \frac{\sigma_{ext}^2}{\langle n\rangle_t^2} + \frac{2[(N-1)C'(t)+(N-2)C'(2t)+\ldots+C'(Nt-t)]}{N^2\langle n\rangle_t^2} =$$

$$\eta_{Nt,init}^2 + \eta_{Nt,ext}^2 + C''(Nt)$$

Eq. S19 shows that the total noise in the number of molecules produced at a particular time window is the sum of the intrinsic noise $\eta^2_{Nt,int}$, extrinsic noise $\eta^2_{Nt,ext}$, and noise resulting from the correlation C"(Nt), which measures the memory effect of the time sequence. When the correlation term and extrinsic noise term are both zero, we have:

$$\frac{\sigma_{Nt}^2}{\langle n\rangle_{Nt}^2} = \frac{1}{N}\frac{\sigma_t^2}{\langle n\rangle_t^2} \propto \frac{1}{N\langle n\rangle_t} = \frac{1}{\langle n\rangle_{Nt}} \quad (S20)$$

This is the pure intrinsic noise.

When the correlation function is a constant without memory, as the cases of $\lambda^{r3}$, $\lambda^b$, and $\lambda^-$ in our observations, we have $$C(t) = \ldots = C(Nt-t) = C$$

$$C = \overline{\langle n(\theta)\rangle^2} - \overline{\langle n(\theta)\rangle}$$

This is the variance of extrinsic noise as in Eq. S15. Therefore, we have $$\eta_{Nt}^2 = \quad (S21)$$

$$\frac{1}{\langle n\rangle_{Nt}}\cdot\frac{\sigma_t^2}{\langle n\rangle_t} + \frac{N(N-1)C}{\langle n\rangle_{Nt}^2} = \frac{1}{\langle n\rangle_{Nt}}\cdot\left(\frac{\sigma_t^2-C}{\langle n\rangle_t}\right) + \frac{C}{\langle n\rangle_t^2} = \frac{A}{\langle n\rangle_{Nt}} + B$$

Here, A is the intrinsic Fano factor (note the subtraction of the extrinsic Fano factor $C/\langle n\rangle t$), and B is the time-independent extrinsic noise. Eq. S21 returns to the commonly seen form where the total noise is simply the sum of intrinsic noise, $\eta^2_{int}$, and extrinsic noise, $\eta^2_{ext}$. Here, the intrinsic noise is inversely proportional to the mean protein production level for the observation time window t and extrinsic noise is a constant independent of mean protein production level[9,12]. Because the mean protein production level for the observation time window t is proportional to t, $\eta^2_{int}$ is inversely proportional to t.

Figure 14A:
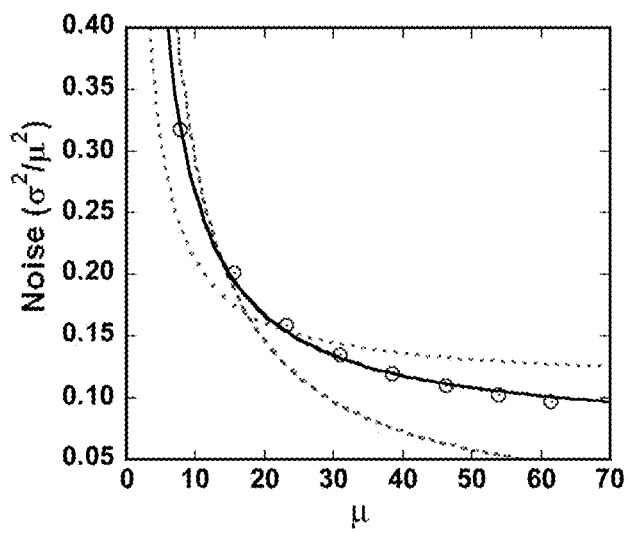
FIG. 14(a) shows a noise curve fitting of strain $\lambda^{r3}$ using one model. The solid black curve is the fitting using Equation 4 in the main text y=A/x+B. The dotted curve is the fitting using equation y=1/x+B by setting the intrinsic Fano factor A at 1. The dashed curve is the fitting using equation y=A/x by setting the extrinsic noise term, B, at 0.
Figure 14B:
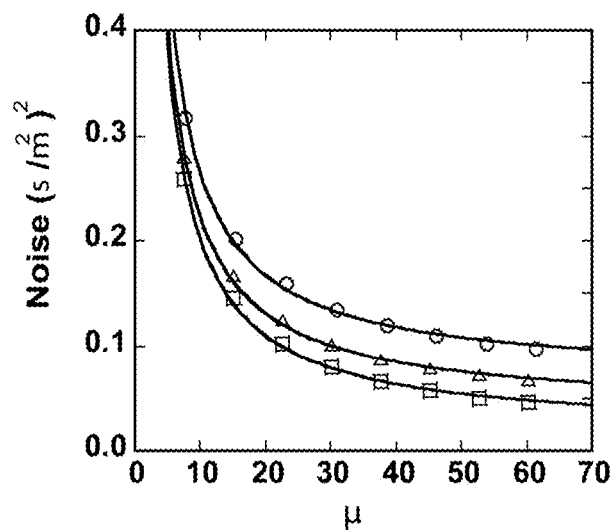
FIG. 14(b) shows the noise curve fitting of strain $\lambda^{r3}$ using a second model, circles denote the noise curve calculated from the entire data set (N=523 cells); triangles are from cells within 1.5 standard deviation of the mean CI production rate per 5-min. (N=464 cells); and squares are from cells within 1 standard deviation (N=377 cells). Solid curves are fits using the equation y=A/x+B. The fitted intrinsic noise, A, changes little (2.9, 2.7 and 2.7 for circles, triangles and squares, respectively). In contrast, the fitted extrinsic noise, B, changes substantially (0.07, 0.04, and 0.02, respectively).
Figure 14C:
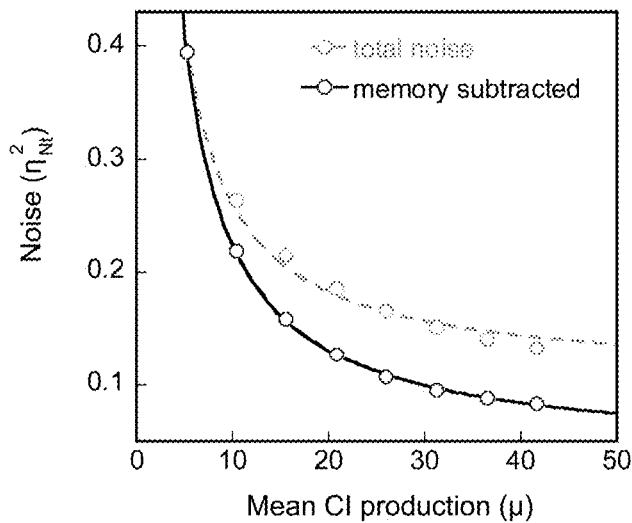
FIG. 14(c) shows the noise curve comparisons for $\lambda^{WT}$. Without subtracting the memory, the resulting noise curve fitting in $\lambda^{WT}$ (dashed gray) is significantly poorer (chi-square increased more than 20-fold) than that with the memory subtracted (solid black).

In FIGS. 14a-c, we plot the noise curve for strain $\lambda^{r3}$. The noise curve is well fit by Eq. S21 (same as Eq. 4 in main text) with an intrinsic Fano factor at 2.9±0.1 and extrinsic noise of 0.07±0.01. We note that the noise curve is poorly fit when the extrinsic noise, B, is fixed at zero, or when the intrinsic Fano factor, A, is fixed at 1 (dashed curves in FIG. 14a). In addition, when we restrict the noise analysis to cells having a mean CI production rate within 1.5 or 1 standard deviation of the total population mean, the fitted intrinsic Fano factor A changes little while extrinsic noise B is reduced substantially (FIG. 14b). This result is consistent with the expectation that intrinsic noise, which is determined by the nature of the biological processes specific to the expression of a specific gene, is unaffected by extrinsic fluctuations; extrinsic noise, a consequence due to static fluctuations in reaction rates from cell to cell, can be reduced by restricting the average protein production range of cells.

In our observations, the strain $\lambda^{wt}$ exhibited significant memory (decreasing autocorrelation over a cell cycle). Therefore, the memory term $C''(Nt)$ can be calculated as:

$$C''(Nt) = \frac{2[(N-1)C'(t) + (N-2)C'(2t) + \ldots + C'(Nt-t)]}{N^2 \langle n \rangle_t^2}$$

Subtracting $C''(Nt)$ from the total noise $\eta^2_{Nt}$: $\eta^2_{Nt} - C''(Nt)$ is the sum of intrinsic and extrinsic noise, which can also be fitted by Eq. S21 to obtain the intrinsic Fano factor A and constant extrinsic noise B. The fitting results for all strains: $\lambda^{r3}$, $\lambda^b$, $\lambda^-$ and $\lambda^{wt}$ are given in Table 1.

3.2 Protein Production Distribution with the Random Bursting Model 3.2.1 Direct Observation of Expression Bursts in a Low-Expression-Level Strain To verify whether random, burst-like production of CI could occur at the $\lambda$ promoter $P_{RN}$, we examined a low-expression-level strain, $\lambda^-$, so that individual bursts may be directly observed. Strain $\lambda^-$ has the same $P_{RM}$ promoter and nearly identical gene sequence compared to that of $\lambda^{r3}$, but encodes a short-lived CI by a point mutation. In $\lambda^-$, there is very little CI because of its shortened lifetime; the Cro protein is expressed and represses $P_{RM}$ (FIG. 2A).

Figure 15:
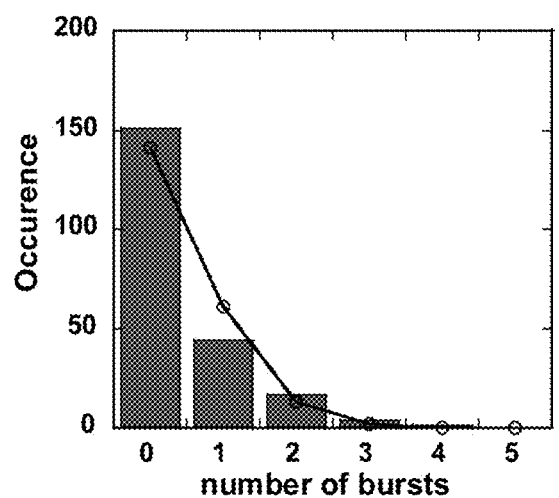
FIG. 15 shows histogram of numbers of bursts in a fixed time window for $\lambda^-$ (N=217 single-generation time traces truncated at 45-min., the shortest cell-cycle time). The histogram was fit with a Poison distribution (solid curve) with an average bursting frequency of ~0.6 burst per cell cycle.

The mean production rate of $\lambda^-$ ($\mu=0.06\pm0.3$, N=2894 from 217 cells) is more than 100-fold less than that of $\lambda^{r3}$, indicating strong repression of $P_{RM}$ by Cro. Consistent with this, we observed small, well-separated expression bursts in $\lambda^-$ (FIG. 2C). The autocorrelation of $\lambda^-$ is also essentially flat across the time scale examined (FIG. 3A). We counted the number of bursts occurred in a fixed time window and found that the distribution can be described by a Poisson distribution with an average bursting frequency of ~0.6 per cell cycle (FIG. 15). The observation is consistent with the expectation that the waiting time between individual bursts is exponentially distributed. The average burst size (including bursts that do not produce any protein molecules) calculated based on the geometric distribution of burst size is 0.47±0.05. The intrinsic Fano factor and extrinsic noise based on the noise curve analysis are 1.8±0.1 and 0.6±0.3, respectively (Table 1).

3.2.2 Master Equations

We use a simplified random bursting model of gene expression in our noise analysis[13-15]. In this model, expression events occur randomly with a given rate, g, with each event instantly producing a burst of protein molecules following a geometric size distribution with a mean of n:

$$G_n = q^n(1-q), \text{ so} \tag{S22}$$

$$\frac{d}{dt}P(n,t) = $$

$$g\left[\sum_{j=1}^{n} G_j P(n-j,t) - qP(n,t)\right] + k(n+1)P(n+1,t) - knP(n,t)$$

Here, $b=q/(1-q)$ is the average burst size, g is the production frequency, and k is the effective degradation rate. The expected distribution of the concentration of molecules in individual cells has been solved previously[14]. The concentration distribution is the balanced result of the production and effective degradation (dilution by cell division and degradation). Our experiments monitor the production of protein molecules; hence, we are interested in the distribution of the number of protein molecules produced during a particular observation time window, t. We note that the probability distribution is no longer dependent on the effective degradation processes, but instead depends on the time t: P(n,t). Therefore, in the master equation for the production process we set the effective degradation rate k=0:

$$\frac{d}{dt}P(n,t) = g\left[\sum_{j=1}^{n} G_j P(n-j,t) - qP(n,t)\right] \tag{S23}$$

3.2.3 Analytic Solution of Time-Dependent Protein Production Distribution

We define the generation function of the production distribution:

$$P(z,t) = \sum_n P(n,t)z^n \Leftrightarrow P(n,t) = \frac{1}{n!}\frac{d^n}{dz^n}P(z,t)|_{z=0} \tag{S24}$$

The master equations can be converted to one equation for the generation function:

$$\frac{d}{dt}P(z,t) = \tag{S25}$$

$$g[q(1-q)zP(z,t) + q^2(1-q)z^2 + \ldots + q^n(1-q)z^n P(z,t) + $$

$$\ldots - qP(z,t)] = g\left[(1-q)P(z,t)\sum_{n=1}^{\infty}(qz)^n - qP(z,t)\right] =$$

$$g\left[(1-q)P(z,t)\frac{qz}{1-qz} - qP(z,t)\right] =$$

$$-g\frac{(1-q)z}{1-qz}P(z,t) \Rightarrow P(z,t) = \exp\left[-gt\frac{(1-z)q}{1-qz}\right]$$

By defining derivative parameters:

$$\lambda = gqt, \quad \chi = \frac{1-q}{q}\lambda,$$

we express the generation function as:

$$P(z,t) = \exp\left[-\frac{\lambda}{q}\frac{z-1}{z-1/q}\right] =$$

$$\exp\left[-\frac{\lambda}{q}\right]\exp\left[\chi\frac{1}{1-qz}\right] = \exp\left[-\frac{\lambda}{q}\right]\left(1 + \sum_{N=1}^{\infty}\chi^N\frac{1}{(1-qz)^N}\right)$$

We employ the Taylor expansion:

$$\frac{1}{(1-qz)^N} = $$

$$1 + Nqz + \frac{N(N+1)}{2!}(qz)^2 + \ldots + \frac{(N)_n}{n!}(qz)^n + \ldots = \sum_{n=0}^{\infty}\frac{(N)_n}{n!}(qz)^n$$

$$(N)_n = N(N+1)\ldots(N+n-1)$$

We derive the Taylor expansion of the generation function:

$$P(z, t) =$$

$$\exp\left[-\frac{\lambda}{q}\right]\left(1 + \sum_{N=1}^{\infty} \frac{1}{N!}\chi^N\left(\sum_{n=0}^{\infty} \frac{(N)_n}{n!}(qz)^n\right)\right) = \sum_{n=0}^{\infty} P(n,t)z^n \Rightarrow P(n,t) =$$

$$\exp\left[-\frac{\lambda}{q}\right]\left(\sum_{N=1}^{\infty} \frac{1}{N!}\chi^N \frac{(N)_n}{n!}q^n\right) = \exp\left[-\frac{\lambda}{q}\right]\left(\sum_{N=1}^{\infty} \chi^N \frac{(N+n-1)!}{(N-1)!N!n!}q^n\right) =$$

$$\exp\left[-\frac{\lambda}{q}\right]\left(\sum_{N=0}^{\infty} \chi^N \frac{(N+n)!}{(N+1)!N!n!}\right)q^n\chi$$

The definition of Kummer's M confluent hypergeometric function is:

$$M(n+1, 2, \chi) = \sum_{N=0}^{\infty} \frac{(n+1)_N \chi^N}{(2)_N N!} = \sum_{N=0}^{\infty} \frac{(n+N)!\chi^N}{(N+1)!N!n!}$$

We express the production distribution using the Kummer's function:

$$P(n \geq 1, t) = \exp\left[-\frac{\lambda}{q}\right]q^n\chi M(n+1, 2, \chi) = \quad (S26)$$

$$\exp[-gt]q^n[(1-q)gt]M[n+1, 2, (1-q)gt]$$

$$P(n=0, t) = \exp[-gqt]$$

It can be checked that this solution satisfies the initial condition:

$$P(0,t=0)=1, P(n\neq 0, t=0)=0.$$

Another way to derive the generation function in Eq. S25 and the probability distribution in Eq. S26 is as the total number of molecules produced during a time in which a Poisson-distributed number of bursts occur. For a time window t, the Poisson distribution of the number of burst events $n_b$ is:

$$P(n_b, t) = \frac{(gt)^{n_b}}{n_b!}e^{-gt}$$

For each burst, the number of proteins produced follows a geometric distribution. The generation function of a Geometric distribution is:

$$\frac{1-q}{1-qz}$$

Then, the generation function of a Poisson number of geometrically-distributed bursts is:

$$P(z,t) = \sum_{n_b=0}^{\infty} \frac{(gt)^{n_b}}{n_b!}e^{-gt}\left(\frac{1-q}{1-qz}\right)^{n_b} = e^{-gt}e^{gt\frac{1-q}{1-qz}} = \exp\left[-gt\frac{(1-z)q}{1-qz}\right] \quad (S27)$$

This is the same as Eq. S25.

3.2.4 Relationship Between Burst Size and Intrinsic Fano Factor

From the generation function in Eq. S25, we can obtain intrinsic Fano factor for a particular $$t: \langle n \rangle(t) = \frac{d}{dz}P(z,t)\Big|_{z=1} = gt\frac{q}{1-q} = gbt \quad (S28)$$

$$\langle n^2 \rangle(t) = \frac{d^2}{dz^2}P(z,t)\Big|_{z=1} + \langle n \rangle(t) = g^2\left(\frac{q}{1-q}\right)^2 t^2 + 2g\left(\frac{q}{1-q}\right)^2 t + bgt =$$

$$g^2 b^2 t^2 + 2b^2 gt + bgt \Rightarrow \frac{\langle n^2 \rangle(t) - \langle n \rangle^2(t)}{\langle n \rangle^2(t)} =$$

$$\frac{2b^2 gt + bgt}{g^2 b^2 t^2} = \frac{2b+1}{gbt} = \frac{2b+1}{\langle n \rangle(t)}$$

Therefore, the average burst size, b, is related to the intrinsic Fano factor F by F=2b+1.

3.2.5 Burst Size in the Presence of Extrinsic Noise

Eq. S28 does not consider the influence of extrinsic noise. Extrinsic noise can be treated as fluctuations ($\eta_g$ and $\eta_b$ respectively) in the kinetic parameters g and b with distributions p(g) and p(b) respectively[11]:

$$\overline{\langle n \rangle(t)} = \int dg \int db\, p(g)p(b)gbt = \langle g \rangle\langle b \rangle t \quad (S29)$$

$$\overline{\langle n^2 \rangle(t)} = \int dg \int db\, p(g)p(b)[g^2 b^2 t^2 + 2b^2 gt + bgt] =$$

$$\langle g^2 \rangle\langle b^2 \rangle t^2 + 2\langle b^2 \rangle\langle g \rangle t + \langle g \rangle\langle b \rangle t \Rightarrow \frac{\overline{\langle n^2 \rangle(t)} - (\overline{\langle n \rangle(t)})^2}{(\overline{\langle n \rangle(t)})^2} =$$

$$\frac{\langle g^2 \rangle\langle b^2 \rangle t^2 + 2\langle b^2 \rangle\langle g \rangle t + \langle g \rangle\langle b \rangle t - \langle g \rangle^2\langle b \rangle^2 t^2}{\langle g \rangle^2\langle b \rangle^2 t^2} =$$

$$(\eta_b^2\eta_g^2 + \eta_g^2 + \eta_b^2) + \frac{2\langle b^2 \rangle\langle g \rangle + \langle g \rangle\langle b \rangle}{\langle g \rangle^2\langle b \rangle^2 t^2}\frac{1}{t} =$$

$$(\eta_b^2\eta_g^2 + \eta_g^2 + \eta_b^2) + \frac{2(\eta_b^2+1)\langle b \rangle + 1}{\langle n \rangle(t)}$$

Here, the total noise is decomposed into intrinsic and extrinsic parts:

$$\eta_{int}^2 = \frac{2(\eta_b^2+1)\langle b \rangle + 1}{\langle n \rangle(t)} \text{ and } \eta_{ext}^2 = (\eta_b^2\eta_g^2 + \eta_g^2 + \eta_b^2). \quad (S30)$$

Therefore, in the presence of extrinsic noise, the measured intrinsic Fano factor, F, is related to the average burst size b by $$F = 2(\eta_b^2+1)\langle b \rangle + 1. \quad (S31)$$

To estimate how much the average burst size is influenced by extrinsic noise, we assume an extreme condition where all the extrinsic noise comes from the fluctuation in burst size $\eta_b$. Because extrinsic noise of $\lambda^{r3}$, $\lambda^b$ and $\lambda^{wt}$ is less then 0.1, the maximal value of $\eta_b^2$ will then be ~0.1. Therefore, extrinsic noise would change the average burst size by 10% at most. However, in the case of $\lambda^-$, where the extrinsic noise is ~0.6 the burst size of $\lambda^-$ will then be between 0.25 and 0.40.

The geometric burst model is a special case for a memoryless system whose noise curve can be decomposed into intrinsic and extrinsic parts; as shown in Eq. S21:

$$\eta_{tot}^2(t) = \eta_{int}^2(t) + \eta_{ext}^2(t) = \frac{A}{\langle n \rangle_{Nt}} + B, \quad (S32)$$

with $A = 2(\eta_b^2 + 1)\langle b \rangle + 1$, $B = (\eta_b^2 \eta_g^2 + \eta_g^2 + \eta_b^2)$.

3.2.6. Derivation of Protein Burst Size from Transcriptional and Translational Burst Sizes Consider a two-step bursting process in which a geometrically distributed transcriptional burst produces an average of $b_1 = q_1/(1-q_1)$ mRNA molecules per burst, and each mRNA molecule produces a geometrically distributed number of proteins with an average burst size $b_2 = q_2/(1-q_2)$. Since the mRNA lifetime is usually short in bacterial cells and our autocorrelation results imply that the protein production process is essentially memoryless, we assume that these two bursts happen close in time so that the waiting time between them is negligibly short. Thus, using the generation function of Geometric distribution: $(1-q)/(1-qz)$, the effective geometric burst distribution of these two instant burst has the generation function:

$$(1-q_1)\sum_n q_1^n \frac{(1-q_2)^n}{(1-q_2z)^n} = \frac{1}{1-q_1\frac{1-q_2}{1-q_2z}} = \frac{1-q_2z}{1-q_1-q_2z+q_1q_2} = \quad (S33)$$

$$\frac{1}{1-q_1-q_2z+q_1q_2} - q_2z\frac{1}{1-q_1-q_2z+q_1q_2}$$

Expanding in order of z, we get the effective burst size distribution $G_j$:

$$G_{j\geq 1} = (1-q)\left[\frac{1}{1-q_1+q_1q_2}\left(\frac{q_2}{1-q_1+q_1q_2}\right)^j - q_2\frac{1}{1-q_1+q_1q_2}\left(\frac{q_2}{1-q_1+q_1q_2}\right)^{j-1}\right] = \quad (S34)$$

$$(1-q_1)\frac{q_1(1-q_2)}{1-q_1+q_1q_2}\left(\frac{q_2}{1-q_1+q_1q_2}\right)^j = q_1(1-Q)Q^j$$

$$G_{j=0} = \frac{1-q_1}{1-q_1+q_1q_2} = 1 - q_1 Q$$

with:

$$Q = \frac{q_2}{1-q_1+q_1q_2}$$

This is a geometric distribution for $j \geq 1$. Furthermore, the effective master equations can be rewritten as:

$$\frac{d}{dt}P(n,t) = g\left[\sum_{j=1}^n q_1 G'_j P(n-j,t) - q_1 Q P(n,t)\right] + \quad (S35)$$

$$k(n+1)P(n+1,t) - knP(n,t) =$$

$$gq_1\left[\sum_{j=1}^n G'_j P(n-j,t) - QP(n,t)\right] + k(n+1)P(n+1,t) - knP(n,t)$$

There is a new burst frequency $gq_1$, a new geometric distribution $G'_j = Q^j(1-Q)$ for $j \geq 0$ and a new average burst size:

$$B = \frac{Q}{1-Q} = \frac{q_2}{(1-q_1)(1-q_2)} = (1+b_1)b_2 \quad (S36)$$

Eq. S35 shows that by modifying the bursting frequency $g$ to $gq_1$, the effective burst size distribution for sequential geometrically distributed bursts with no time interval between them is still a geometric distribution, and the average burst size can be calculated according to Eq. S36. In Eq. S28, we show that for the random burst model the intrinsic Fano factor, A, is related to the average burst size, $b$, by $A \approx 2b+1$. Using this equation and the intrinsic Fano factor obtained from noise curve analysis, we calculated burst sizes of $0.40 \pm 0.06$ and $0.95 \pm 0.04$ for $\lambda^-$ and $\lambda^{r3}$, respectively. The random bursting model does not distinguish translational bursting from transcriptional bursting as long as the final protein burst size follows a geometric distribution. Assuming that there are geometric transcriptional and translational bursts with average burst sizes of $b_1$ and $b_2$ respectively, in Eq. S36, we show that the combined process can still be treated as a single bursting step with a final geometric protein burst size $b = (1+b_1)b_2$. Because the transcripts in $\lambda^-$ and $\lambda^{r3}$ are essentially identical in sequence, we assume that the average translational burst size $b_2$ is identical for both strains. Therefore, we obtain the average transcriptional burst size of $$\lambda^{r3} b_1^{r3} = \frac{b^{r3}}{b^-}(1+b_1^-) - 1 \approx 1.4 + 2.4 b_1^-$$

where $b_1^-$ is the transcriptional burst size of $\lambda^-$. If transcription in $\lambda^-$ is Poissonian (e.g. $b_1^- = 0$, a reasonable assumption for a strongly repressed promoter[1]), the average transcriptional burst size of $\lambda^{r3}$ will still be greater than zero, suggesting the presence of transcriptional bursting in $\lambda^{r3}$.

3.3 Additional Considerations

3.3.1 Influence of Fluorescent Protein Maturation on Noise Analysis

Fluorescent proteins generally mature slowly (tens of minutes to hours) to become fluorescent. The YFP variant, Venus, used in the work is the fastest maturing fluorescent protein to date—it was reported to mature with a half-time of ~2-7 min[1,16]. Since only fluorescent protein molecules can be counted and photobleached, the post-translational maturation process will inevitably add one more level of noise to the transcription and translation processes. We evaluate how maturation influences the total noise in the measurements of protein production and show that fast maturation does not significantly impact our noise analysis.

Influence of Maturation on Total Noise and Burst Size

Using $n_1$ to indicate the number of immature (unobservable) Venus molecules and $n_2$ to indicate mature (observable) Venus molecules, the master equation for the production process including maturation with first-order reaction kinetics is:

$$\frac{dP(n_1, n_2, t)}{dt} = g\left[\sum_{j=1}^n G_j P(n_1 - j, n_2, t) - qP(n_1, n_2, t)\right] + \quad (S37)$$

$$\beta[(n_1+1)P(n_1+1, n_2-1, t) - n_1 P(n_1, n_2, t)]$$

Here β is the rate of maturation. There is no analytical solution for this equation. However, following the moment equations for concentration in the steady state[17], we can solve the analytic noise expression for the production only:

$$\langle n_1 \rangle = \frac{gb}{\beta}, \quad \langle n_1^2 \rangle = \langle n_1 \rangle^2 + \langle n_1 \rangle (b+1), \quad \langle n_2 \rangle = gbt$$

$$d\langle n_2^2 \rangle / dt = \beta(2\langle n_1 n_2 \rangle + \langle n_1 \rangle)$$

$$d\langle n_1 n_2 \rangle / dt = gb\langle n_2 \rangle + \beta(-\langle n_1 n_2 \rangle + \langle n_1^2 \rangle - \langle n_1 \rangle)$$

$$\langle n_2^2 \rangle (t=0) = 0, \quad \langle n_1 n_2 \rangle (t=0) = 0$$

The solution follows the direct algebra:

$$\langle n_2^2 \rangle(t) = g^2 b^2 t^2 + gbt(2b+1) + \frac{1}{\beta}[2gb^2(e^{-\beta t}-1)] \quad (S39)$$

$$\eta_{n_2}^2 = \frac{2b+1}{gbt} + \frac{1}{gbt}\frac{2b(e^{-\beta t}-1)}{\beta t}$$

Furthermore, with the extrinsic fluctuations on the kinetic parameters g and b, the analytic noise expression is given as follows:

$$\eta_{n_2}^2 = (\eta_b^2 \eta_g^2 + \eta_g^2 + \eta_b^2) + \frac{2(\eta_b^2+1)\langle b \rangle + 1}{\langle g \rangle \langle b \rangle t} + \quad (S40)$$

$$\frac{2}{\langle g \rangle \langle b \rangle t}(\eta_b^2+1)\langle b \rangle \frac{(e^{-\beta t}-1)}{\beta t}$$

$$= B + \frac{C+1}{\langle g \rangle \langle b \rangle t} + \frac{C}{\langle g \rangle \langle b \rangle t}\frac{(e^{-\beta t}-1)}{\beta t}$$

$$C = 2(\eta_b^2+1)\langle b \rangle$$

In the limit of infinitely fast maturation (β=∞):

$$\eta_{n_2}^2 = B + \frac{C+1}{\langle g \rangle \langle b \rangle t} = \frac{A}{\langle n \rangle_t} + B$$

This is the previous result of Eq. S32 a complete memoryless system. In a system where the maturation process is slow, the real protein burst b is related to the observed noise by:

$$b = \frac{(\langle n(t) \rangle \eta_{tot}^2 - \langle n(t) \rangle \eta_{est}^2 - 1)/2}{1 + \frac{(e^{-\beta t}-1)}{\beta t}} \quad (S41)$$

This will be larger than that the apparent burst if maturation were ignored. However, the correction factor (the denominator of Eq. S41) is the same for all strains with the same fluorescent reporter.

Figure 16A:
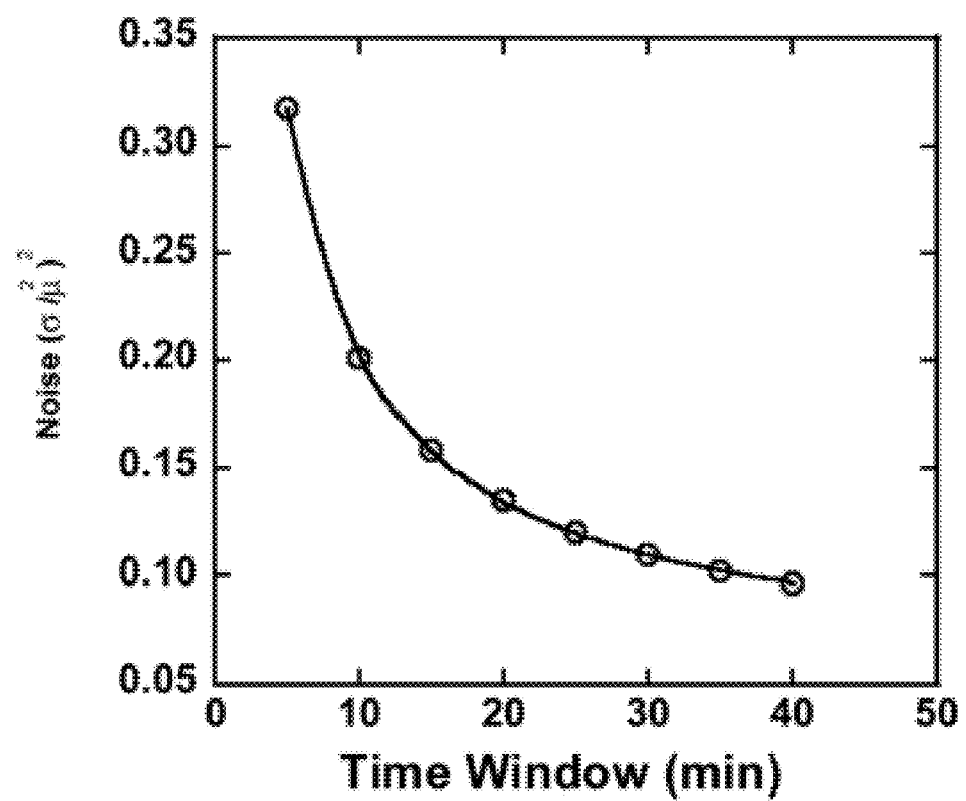
FIG. 16(a) is a noise curve fitting by considering the maturation effect for strain $\lambda^{r3}$ The circles are the noise at each time window and the solid curve is the fitting using Eq. S40. The fit values are reported in Table S5.
Figure 16B:
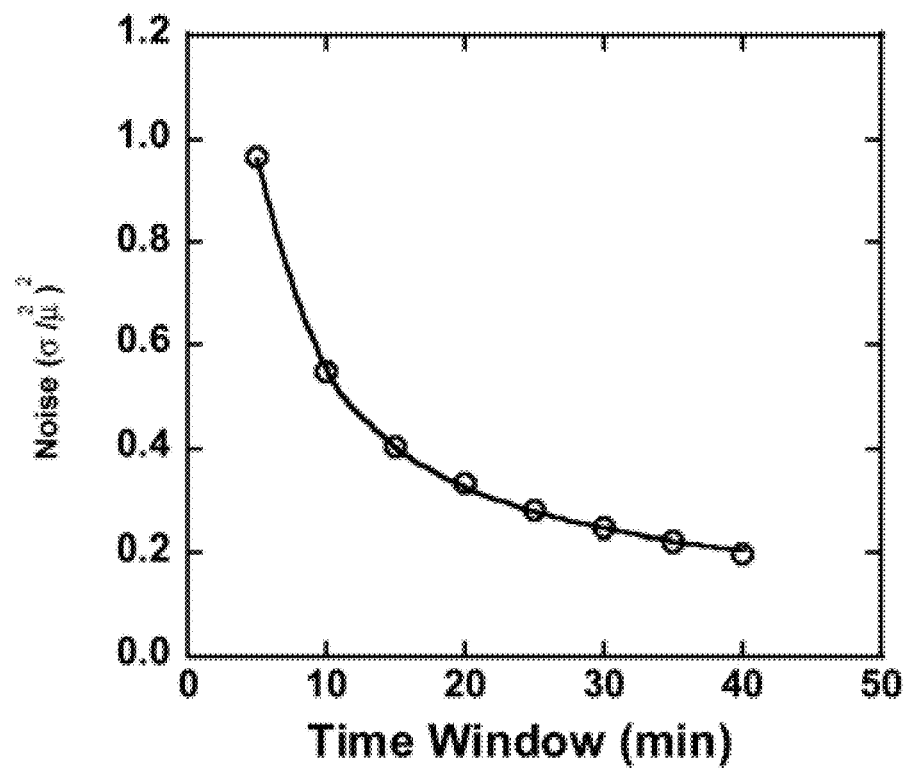
FIG. 16(b) is a noise curve fitting by considering the maturation effect for strain $\lambda^b$. The circles are the noise at each time window and the solid curve is the fitting using Eq. S40. The fit values are reported in Table S5.
Figure 16C:
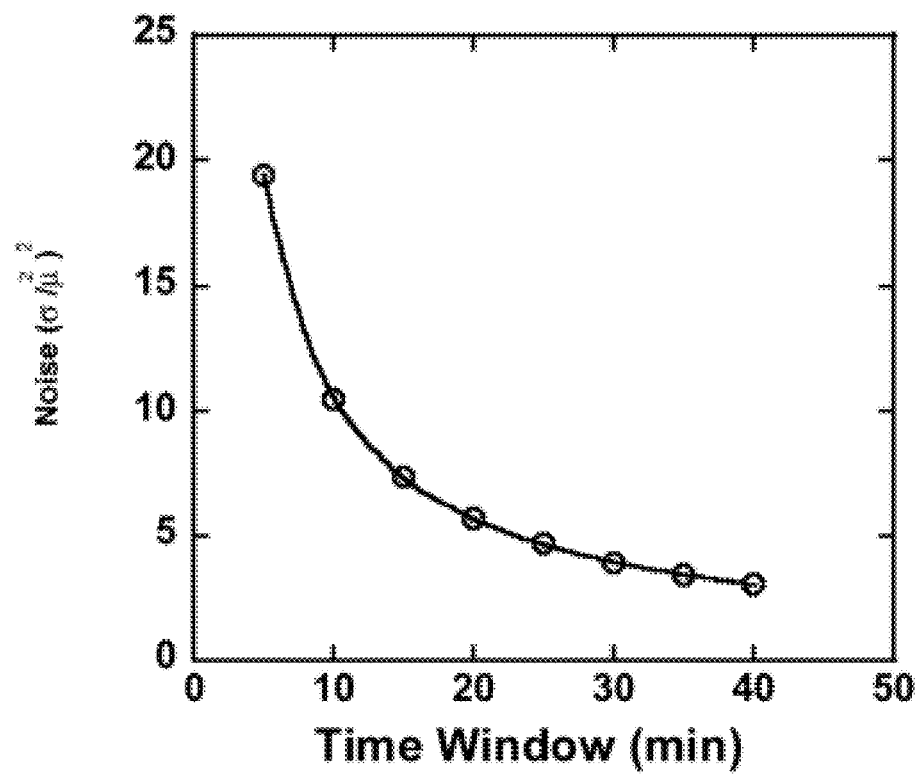
FIG. 16(c) is a noise curve fitting by considering the maturation effect for strain $\lambda^-$. The circles are the noise at each time window and the solid curve is the fitting using Eq. S40. The fit values are reported in Table S5.

We used Eq. S40 to fit the noise curves of $\lambda^{r3}$, $\lambda^-$ and $\lambda^b$ (FIGS. 16a-c and Table S5). We found that including the additional maturation term does not significantly improve fitting goodness. The average fit maturation time constant, τ, ranges from 1.3 to 3.4 min., consistent with reports of fast Venus maturation {Nagai, 2002 #316; Yu, 2006 #673}. The resulting burst size for each strain ($\lambda^{r3}$, $\lambda^-$ and $\lambda^b$) is larger than that by ignoring maturation. However, the trend of the burst size between these strains is unchanged.

Influence of Maturation on Autocorrelation

If maturation is the rate-limiting step of the entire process including transcription and translation, the autocorrelation of the protein production time traces of single generations will have higher correlation values at short time lags compared to long time lags. This is because the maturation process is not memoryless and will spread a single burst of protein production into a few adjacent frames. We did not observe significant correlation above a constant plateau at the shortest time lag, 5 min., and the correlation after that is essentially flat for the $\lambda^{r3}$, $\lambda^-$ and $\lambda^b$ strains. This result indicates that the maturation rate is at least faster than our time resolution of 5 min., consistent with the noise curve analysis.

3.3.2 the Effect of False Negatives in Single-Molecule Counting

Suppose that each fluorescent molecule has a chance p of being missed in the observation. Given this binomial sampling error, the probability of observing m molecules out of a total n molecules is:

$$P(m|n) = C_n^m p^m (1-p)^{n-m}$$

Thus, the total probability of observing m molecules is:

$$P(m) = \sum_{n \geq m} P(m|n)P(n) = \sum_{n \geq m} C_n^m p^m (1-p)^{n-m} P(n)$$

Here, P(n) is the distribution of the total number of molecules in a cell. We consider the generation function of observing m molecules:

$$G(x) = \sum_m P(m) x^m =$$

$$\sum_n \left[ \sum_m C_n^m p^m (1-p)^{n-m} x^m \right] P(n) = \sum_n [px + (1-p)]^n P(n) = \overline{P}(\overline{z})$$

$$\overline{z} = px + (1-p)$$

Here, $\overline{P}(\overline{z})$ is the generation function of total molecule distribution. For the production distribution of the geometric burst model, $\overline{P}(\overline{z})$ is the generation function as in Eq. S25, so:

$$G(x,t) = \exp\left\{-gt \frac{q[1-(px+1-p)]}{1-q[px+1-p]}\right\} = \exp\left[-gt \frac{\overline{q}(1-x)}{1-\overline{q}x}\right] \quad (S42)$$

$$\overline{q} = \frac{pq}{1-q(1-p)}$$

It means that the distribution of observed molecules has the same form as that of the total number of molecules in the cell as in Eq. S26, but with a modified observable burst size $\overline{b}$:

$$\overline{b} = pb \quad (S43)$$

Here, b is the true average burst size in the cell. Similarly for the steady state distribution of concentrations, the generation function $\overline{P}(\overline{z})$ for the negative binomial distribution is:

$$\bar{P}(\bar{z}) = \left(\frac{1-q}{1-q\bar{z}}\right)^{g/k}$$

So the generation function of observed molecules is:

$$G(x) = \left(\frac{1-\bar{q}}{1-\bar{q}x}\right)^{g/k} \quad (S44)$$

$$\bar{q} = \frac{pq}{1-q(1-p)}$$

This means that the distribution of the observed steady state distribution of the concentration has the same negative binomial distribution form as the total steady state distribution, but a modified burst size:

$$\bar{b} = pb \quad (S45)$$

In conclusion, false negatives arising from effects such as early photobleaching will not change the form of the distribution, but will change the burst size and the effect will be the same for all strains.

3.3.3 Influence of Cell Division Noise on the Protein Production Noise

In our experiments, we directly measure protein production rather than concentration. Therefore, our noise measurement is less influenced by noise introduced by protein degradation and errors in protein partitioning during cell division, as detailed in a previous analysis[18]. However, mRNA molecules are still subject to degradation and partitioning errors, which will inevitably introduce noise in the subsequent protein production process according to the following equation[18]:

$$\eta_m^2 = \left[1 + \frac{e^{-2t/\tau_m}}{4 - e^{-2T/\tau_m}} \frac{t}{T} \frac{1 - e^{-T/\tau_m}}{1 - e^{-t/\tau_m}} \frac{2 - e^{-t/\tau_m}}{2 - e^{-T/\tau_m}} (A_y - 1)\right] \frac{1}{\langle m \rangle} \quad (S46)$$

Here, $\tau_m$ is the life time of mRNA, $A_y$ is the cell division partition error, T is the cell life time, t is the time of the measurement relative to the beginning of the cell cycle. In our experiments, given the average cell cycle time of 65 min, an observation interval of 5 min., and assuming short mRNA life time, $\tau_m \sim 1\text{-}2$ min., we obtain:

$$\eta_m^2 \approx \frac{1}{\langle m \rangle}. \quad (S47)$$

This indicates that for mRNA molecules having short life times, the noise in mRNA copy number distribution won't be significantly affected by the cell division partition error. Therefore, partitioning error at cell division should have minimal effect on protein production noise.

Supplementary Tables

TABLE S1

| | Bacterial strains | |
|---|---|---|
| Strain | Genotype | Source |
| JL5392 | JL2497 lysogenized with JL163 | Gift from John Little |
| $\lambda^{wt}$ | MG1655 (cl-rexB)::tsr-venus-ub-cl/pCG001 | This work |

TABLE S1-continued

| | Bacterial strains | |
|---|---|---|
| Strain | Genotype | Source |
| $\lambda^{r3}$ | $\lambda^{wt}$ $O_R$3-r3/pCG001 | This work |
| $\lambda^{b}$ | $\lambda^{wt}$ clM1L $\Delta$cro | This work |
| $\lambda^{-}$ | $\lambda^{wt}$ clM1L/pCG001 | This work |

TABLE S2

| Primer | Sequence |
|---|---|
| P1 | gacgatggatccgggctggaatgtgtaagagc |
| P2 | Gattggatcctgcgtcctgctgaggtgc |
| P3 | Catagcaattcagatctctcacctac |
| P4 | Atgcgccgaccagaacac |
| P5 | Gcatactcgagatgcagatttcgtcaagac |
| P6 | accacctcttagccttagcacaagatgtaagg |
| P7 | Atgagcacaaaaaagaaaccattaacac |
| P8 | Ctatctcgagttaaatctatcaccgcaag |
| P9 | cgggctcgagaggaaacagctatgttaaaacgtatc |
| P10 | Ctaacccggggtgtaggctggagctgcttc |
| P11 | catacccgggaaccatctgcggtgataaattatc |
| P12 | cattctcgagtatcaccgcaagggataaatatctaac |
| P13 | Caatacgcaaaccgcctctc |
| P14 | Ggctgcggtagttcaggcag |
| P15 | gcacggtgttagatatttatcccttgtggtgatagatttaac |
| P16 | gttaaatctatcaccacaagggataaatatctaacaccgtgc |
| P17 | tgctaaggctaagagtgtgtctgagcacaaaaaagaaac |
| P18 | acgattccgattctccaccagactcgtgttttttctttg |
| P19 | tgtactaaggaggttgtatgaacaacgcataaccctgaaa |
| P20 | tttcagggttatgcgttgttcatacaacctccttagtaca |
| P21 | Agcaagggcgaggagctgt |
| P22 | Catagctgtttcctgtgtgctcg |

TABLE S3

Noise is unaffected by correcting the CI production rate for the cell-cycle effect. The data below were calculated using either uncorrected raw or linearly corrected time traces of CI production in 5-min. frames.

| | | $\lambda^{r3}$ | $\lambda^{-}$ | $\lambda^{b}$ | $\lambda^{wt}$ |
|---|---|---|---|---|---|
| Uncorrected data | $\mu$ | 11.6 | 0.095 | 2.9 | 7.7 |
| | $\sigma^2/\mu^2$ | 0.32 | 18.3 | 0.96 | 0.40 |
| | $\sigma^2/\mu$ | 3.7 | 1.7 | 2.8 | 3.0 |
| Corrected data | $\mu$ | 7.8 | 0.063 | 1.9 | 5.2 |
| | $\sigma^2/\mu^2$ | 0.32 | 19.4 | 0.96 | 0.39 |
| | $\sigma^2/\mu$ | 2.5 | 1.2 | 1.9 | 2.0 |
| | 1.44 $\sigma^2/\mu$ | 3.6 | 1.8 | 2.7 | 3.0 |

TABLE S4

Noise properties of the four strains. All results are calculated using cell-cycle-corrected data.

| | | $\lambda^{r3}$ | $\lambda^-$ | $\lambda^b$ | $\lambda^{wt}$ |
|---|---|---|---|---|---|
| | Total noise | 0.32 | 19.4 | 0.96 | 0.40 |
| Intrinsic noise estimated from | noise curve | 0.25 | 19.0 | 0.87 | 0.36 |
| | correlation pairs | 0.22 | 18.7 | 0.81 | 0.25 |
| | cell-cycle average | 0.23 | 17.2 | 0.80 | 0.27 |
| | Intrinsic Fano factor | 2.9 | 1.8 | 2.4 | 2.7 |
| Extrinsic noise estimated from | autocorrelation | 0.09 | 0.6 | 0.10 | 0.08 |
| | noise curve | 0.07 | 0.6 | 0.10 | 0.04 |
| | correlation pairs | 0.09 | 1.1 | 0.13 | 0.14 |
| | cell-cycle average | 0.09 | 2.2 | 0.16 | 0.13 |

TABLE S5

Noise curve fitting with maturation using Eq. S40.

| | $\lambda^-$ | $\lambda^b$ | $\lambda^{r3}$ |
|---|---|---|---|
| Extrinsic noise | 0.25 | 0.08 | 0.06 |
| Burst size | 0.54 | 0.91 | 1.31 |
| Maturation time (min) | 3.4 | 1.3 | 1.7 |

The invention has been described with references to a preferred embodiment. While specific values, relationships, materials and steps have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

REFERENCES

The following references are incorporated herein by reference in their entirety.

1. Taniguchi, Y., et al., Quantifying E. coli proteome and transcriptome with single-molecule sensitivity in single cells. Science. 329(5991): p. 533-8. (2010)
2. Pedraza, J. M. and van Oudenaarden, A., Noise propagation in gene networks. Science. 307(5717): p. 1965-9. (2005)
3. Rosenfeld, N., et al., Gene regulation at the single-cell level. Science. 307(5717): p. 1962-5. (2005)
4. Shen-Orr, S. S., et al., Network motifs in the transcriptional regulation network of Escherichia coli. Nat. Genet. 31(1): p. 64-8. Epub 2002 Apr. 22. (2002)
5. Yu, J., et al., Probing gene expression in live cells, one protein molecule at a time. Science. 311(5767): p. 1600-3. (2006)
6. Ptashne, M., A genetic switch: Phage lambda revisited. 3rd ed. 2004, Cold Spring Harbor, N.Y.: Cold Spring Harbor Laboratory Press.
7. Tobias, J. W., et al., The N-end rule in bacteria. Science. 254(5036): p. 1374-7. (1991)
8. Pedraza, J. M. and Paulsson, J., Effects of molecular memory and bursting on fluctuations in gene expression. Science. 319(5861): p. 339-43. (2008)
9. Meyer, B. J., Maurer, R., and Ptashne, M., Gene regulation at the right operator (OR) of bacteriophage lambda. II. OR1, OR2, and OR3: their roles in mediating the effects of repressor and cro. J Mol. Biol. 139(2): p. 163-94. (1980)
10. Sarai, A. and Takeda, Y., Lambda repressor recognizes the approximately 2-fold symmetric half-operator sequences asymmetrically. Proc Natl Acad Sci USA. 86(17): p. 6513-7. (1989)
11. Levine, A., Bailone, A., and Devoret, R., Cellular levels of the prophage lambda and 434 repressors. J Mol. Biol. 131(3): p. 655-61. (1979)
12. Reichardt, L. and Kaiser, A. D., Control of lambda repressor synthesis. Proc Natl Acad Sci USA. 68(9): p. 2185-9. (1971)
13. Wang, J. and Wolynes, P., Intermittency of single molecule reaction dynamics in fluctuating environments. Phys Rev Lett. 74(21): p. 4317-4320. (1995)
14. Ozbudak, E. M., et al., Regulation of noise in the expression of a single gene. Nat. Genet. 31(1): p. 69-73. (2002)
15. Golding, I., et al., Real-time kinetics of gene activity in individual bacteria. Cell. 123(6): p. 1025-36. (2005)
16. Huh, D. and Paulsson, J., Non-genetic heterogeneity from stochastic partitioning at cell division. Nat. Genet. 43(2): p. 95-100. (2010)
17. Elowitz, M. B., et al., Stochastic gene expression in a single cell. Science. 297(5584): p. 1183-6. (2002)
18. Swain, P. S., Elowitz, M. B., and Siggia, E. D., Intrinsic and extrinsic contributions to stochasticity in gene expression. Proc Natl Acad Sci USA. 99(20): p. 12795-800. (2002)
19. Hilfinger, A. and Paulsson, J., Separating intrinsic from extrinsic fluctuations in dynamic biological systems. Proc Natl Acad Sci USA. (2011)
20. Raj, A., et al., Stochastic mRNA synthesis in mammalian cells. PLoS Biol. 4(10): p. e309. (2006)
21. So, L. H., et al., General properties of transcriptional time series in Escherichia coli. Nat. Genet. 43(6): p. 554-60. (2011)
22. Shahrezaei, V. and Swain, P. S., Analytical distributions for stochastic gene expression. Proc Natl Acad Sci USA. 105(45): p. 17256-61. (2008)
23. Zenklusen, D., Larson, D. R., and Singer, R. H., Single-RNA counting reveals alternative modes of gene expression in yeast. Nat Struct Mol. Biol. 15(12): p. 1263-71. (2008)
24. Suter, D. M., et al., Mammalian genes are transcribed with widely different bursting kinetics. Science. 332(6028): p. 472-4. (2011)
25. Hornos, J. E., et al., Self-regulating gene: an exact solution. Phys Rev E Stat Nonlin Soft Matter Phys. 72(5 Pt 1): p. 051907. Epub 2005 Nov. 4. (2005)
26. Lepzelter, D., Kim, K. Y., and Wang, J., Dynamics and Intrinsic Statistical Fluctuations of a Gene Switch. J Phys Chem B. (2007)

27. Feng, H., Han, B., and Wang, J., Adiabatic and non-adiabatic non-equilibrium stochastic dynamics of single regulating genes. J Phys Chem B. 115(5): p. 1254-61. (2011)
28. Feng, H. and Wang, J., Landscape and global stability of non-adiabatic and adiabatic oscillations in a gene network. Biophys. J. 102: p. 1001. (2012)
29. Choi, P. J., et al., A stochastic single-molecule event triggers phenotype switching of a bacterial cell. Science. 322(5900): p. 442-6. (2008)
30. Singh, A. and Weinberger, L. S., Stochastic gene expression as a molecular switch for viral latency. Curr Opin Microbiol. 12(4): p. 460-6. (2009)
31. Kalmar, T., et al., Regulated fluctuations in nanog expression mediate cell fate decisions in embryonic stem cells. PLoS Biol. 7(7): p. e1000149. (2009)
32. Feng, H. and Wang, J., A new formulation of two-time correlation functions of Markov chains applied to gene networks. Chemical Physics Letters. 501(4-6): p. 562-566. (2011)
33. Lu, T., Hasty, J., and Wolynes, P. G., Effective temperature in stochastic kinetics and gene networks. Biophys J. 91(1): p. 84-94. (2006)
34. Dodd, I. B., et al., Cooperativity in long-range gene regulation by the lambda CI repressor. Genes Dev. 18(3): p. 344-54. (2004)
35. Bar-Even, A., et al., Noise in protein expression scales with natural protein abundance. Nat. Genet. 38(6): p. 636-43. (2006)
36. Zong, C., et al., Lysogen stability is determined by the frequency of activity bursts from the fate-determining gene. Mol Syst Biol. 6: p. 440. (2011)
37. Wang, J., Statistics, pathways and dynamics of single molecule protein folding. J. Chem. Phys. 118: p. 952-58. (2003)
38. Ross, S. M., *Stochastic Processes*. 1983, New York: John Wiley & Sons.
39. Cai, L., Friedman, N., and Xie, X. S., Stochastic protein expression in individual cells at the single molecule level. Nature. 440(7082): p. 358-62. (2006)
40. Hawley, D. K. and McClure, W. R., Mechanism of activation of transcription initiation from the lambda PRM promoter. J Mol. Biol. 157(3): p. 493-525. (1982)
41. Datsenko, K. A. and Wanner, B. L., One-step inactivation of chromosomal genes in *Escherichia coli* K-12 using PCR products. Proc Natl Acad Sci USA. 97(12): p. 6640-5. (2000)
42. Tobias, J. W. and Varshaysky, A., Cloning and functional analysis of the ubiquitin-specific protease gene UBP1 of *Saccharomyces cerevisiae*. J Biol. Chem. 266(18): p.

What is claimed is:

1. A method for measuring expression of an autoregulatory molecule, comprising:

expressing a construct in a cell, wherein the construct comprises a purified and isolated polynucleotide, comprising a polynucleotide sequence encoding an autoregulatory molecule, a polynucleotide sequence encoding a measurable marker, and a polynucleotide sequence encoding a cleavable substrate, wherein the polynucleotide sequence encoding the cleavable substrate connects the polynucleotide sequence encoding the autoregulatory molecule and the polynucleotide sequence encoding the measurable marker;

expressing a protease capable of cleaving the cleavable substrate in the cell, wherein the protease cleaves the cleavable substrate during translation allowing the autoregulatory molecule to fold into a functional molecule; and evaluating the cell for the presence of the measurable substrate.

2. The method of claim 1, wherein the cell is an *E. coli* cell.

3. The method of claim 1, wherein the autoregulatory molecule is CI.

4. The method of claim 1, wherein the measurable marker is selected from the group consisting of fluorescent peptides, colorimetric compounds, chemiluminescent peptides, and combinations thereof.

5. The method of claim 4, where the fluorescent peptide is selected from the group consisting of yellow fluorescent protein (YFP), blue fluorescent protein (BFP), green fluorescent protein (GFP), red fluorescent protein (RFP) and fluorescing mutants thereof.

6. A purified and isolated polynucleotide, comprising
a polynucleotide sequence encoding an autoregulatory molecule,
a polynucleotide sequence encoding a measurable marker, and
a polynucleotide sequence encoding a cleavable substrate, wherein the polynucleotide sequence encoding the cleavable substrate connects the polynucleotide sequence encoding the autoregulatory molecule and the polynucleotide sequence encoding the measurable marker, and wherein upon translation of the polynucleotide, when expressed in a cell, the cleavable substrate is cleaved by a protease releasing the measurable marker and allowing the autoregulatory molecule to fold functionally.

* * * * *

SEQUENCE LISTING

```
<160> NUMBER OF SEQ ID NOS: 22

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
gacgatggat ccgggctgga atgtgtaaga gc                                   32

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
gattggatcc tgcgtcctgc tgaggtgc                                        28

<210> SEQ ID NO 3
<211> LENGTH: 26
<212> TYPE: DNA
<213> ORGANISM: Artificial Sequence
<220> FEATURE:
<223> OTHER INFORMATION: Primer

<400> SEQUENCE: 3
catagcaatt cagatctctc acctac                                          26

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
```
atgcgccgac cagaacac	18

<210> SEQ ID NO 5
<211> LENGTH: 31
<212> TYPE: DNA
<213> ORGANISM: Artificial Sequence
<220> FEATURE:
<223> OTHER INFORMATION: Primer

<400> SEQUENCE: 5
gcatactcga gatgcagatt ttcgtcaaga c	31

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6
accacctctt agccttagca caagatgtaa gg	32

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
atgagcacaa aaagaaacc attaacac	28

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
ctatctcgag ttaaatctat caccgcaag	29

<210> SEQ ID NO 9
<211> LENGTH: 36
<212> TYPE: DNA
<213> ORGANISM: Artificial Sequence
<220> FEATURE:
<223> OTHER INFORMATION: Primer

<400> SEQUENCE: 9
cgggctcgag aggaaacagc tatgttaaaa cgtatc	36

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
ctaacccggg gtgtaggctg gagctgcttc	30

<210> SEQ ID NO 11
<211> LENGTH: 34
<212> TYPE: DNA

```
<213> ORGANISM: Artificial Sequence
<220> FEATURE:
<223> OTHER INFORMATION: Primer

<400> SEQUENCE: 11
catacccggg aaccatctgc ggtgataaat tatc                          34

<210> SEQ ID NO 12
<211> LENGTH: 37
<212> TYPE: DNA
<213> ORGANISM: Artificial Sequence
<220> FEATURE:
<223> OTHER INFORMATION: Primer

<400> SEQUENCE: 12
cattctcgag tatcaccgca agggataaat atctaac                       37

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
caatacgcaa accgcctctc                                          20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ggctgcggta gttcaggcag                                          20

<210> SEQ ID NO 15
<211> LENGTH: 42
<212> TYPE: DNA
<213> ORGANISM: Artificial Sequence
<220> FEATURE:
<223> OTHER INFORMATION: Primer

<400> SEQUENCE: 15
gcacggtgtt agatatttat cccttgtggt gatagattta ac                 42

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
gttaaatcta tcaccacaag ggataaatat ctaacaccgt gc                 42

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
tgctaaggct aagagtgtgt ctgagcacaa aaaagaaac                     39
```

```
<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18
acgattccga ttctccacca gactcgtgtt ttttctttg                                    39

<210> SEQ ID NO 19
<211> LENGTH: 40
<212> TYPE: DNA
<213> ORGANISM: Artificial Sequence
<220> FEATURE:
<223> OTHER INFORMATION: Primer

<400> SEQUENCE: 19
tgtactaagg aggttgtatg aacaacgcat aaccctgaaa                                   40

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
tttcagggtt atgcgttgtt catacaacct ccttagtaca                                   40

<210> SEQ ID NO 21
<211> LENGTH: 19
<212> TYPE: DNA
<213> ORGANISM: Artificial Sequence
<220> FEATURE:
<223> OTHER INFORMATION: Primer

<400> SEQUENCE: 21
agcaagggcg aggagctgt                                                          19

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
catagctgtt tcctgtgtgc tcg                                                     23
```